(12) United States Patent
Yoshimine

(10) Patent No.: US 9,730,710 B2
(45) Date of Patent: Aug. 15, 2017

(54) ULTRASONIC PROBE AND ULTRASONIC INSTRUMENT

(71) Applicant: OLYMPUS CORPORATION, Hachioji-shi, Tokyo (JP)

(72) Inventor: Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/332,550

(22) Filed: Oct. 24, 2016

(65) Prior Publication Data

US 2017/0035454 A1    Feb. 9, 2017

Related U.S. Application Data

(63) Continuation of application No. PCT/JP2015/076188, filed on Sep. 15, 2015.

(30) Foreign Application Priority Data

Jan. 7, 2015    (JP) .................................. 2015-001840

(51) Int. Cl.
*A61B 17/32* (2006.01)
*A61B 17/16* (2006.01)
(Continued)

(52) U.S. Cl.
CPC .......... *A61B 17/1684* (2013.01); *A61B 17/16* (2013.01); *A61B 17/1778* (2016.11);
(Continued)

(58) Field of Classification Search
CPC ............ A61B 17/320068; A61B 2017/320008
See application file for complete search history.

(56) References Cited

U.S. PATENT DOCUMENTS 5,205,817 A * 4/1993 Idemoto ......... A61B 17/320068
                                                   604/22
6,283,981 B1 * 9/2001 Beaupre ......... A61B 17/320068
                                                   606/169

(Continued)

FOREIGN PATENT DOCUMENTS

JP    2005-152098 A    6/2005
JP    2007-531563 A    11/2007
JP    2014-533148 A    12/2014

OTHER PUBLICATIONS

Dec. 8, 2015 International Search Report issued in International Patent Application No. PCT/JP2015/076188.

*Primary Examiner* — Andrew Yang
(74) *Attorney, Agent, or Firm* — Oliff PLC

(57) ABSTRACT

The ultrasonic probe for a shoulder joint includes a curved extending section curved to a probe main body toward a first intersecting direction intersecting a longitudinal axis. The curved extending section includes a first curved outer surface facing the first intersecting direction, a second curved outer surface facing a second intersecting direction opposite of the first intersecting direction, a third curved outer surface facing a first width direction perpendicular to the first and second intersecting directions, and a fourth curved outer surface facing a second width direction opposite of the first width direction. A relay groove on a cutting surface in the second curved outer surface is continuous with extending grooves on cutting surfaces in the third curved outer surface and the fourth curved outer surface.

12 Claims, 7 Drawing Sheets

(51) Int. Cl.
*A61B 18/00* (2006.01)
*A61B 17/17* (2006.01)
*A61N 7/00* (2006.01)

(52) U.S. Cl.
CPC .......... *A61B 17/32002* (2013.01); *A61B 17/320068* (2013.01); *A61B 18/00* (2013.01); *A61B 2017/320004* (2013.01); *A61B 2017/320008* (2013.01); *A61B 2017/320052* (2013.01); *A61B 2017/320072* (2013.01); *A61B 2017/320076* (2013.01); *A61N 2007/0043* (2013.01)

(56) References Cited

U.S. PATENT DOCUMENTS

| | | |
|---|---|---|
| 2005/0234484 A1 | 10/2005 | Houser et al. |
| 2013/0103066 A1 | 4/2013 | Rad |
| 2014/0135804 A1 | 5/2014 | Weisenburgh, II et al. |
| 2014/0163595 A1* | 6/2014 | Witt ............... A61B 17/320068 606/169 |

\* cited by examiner

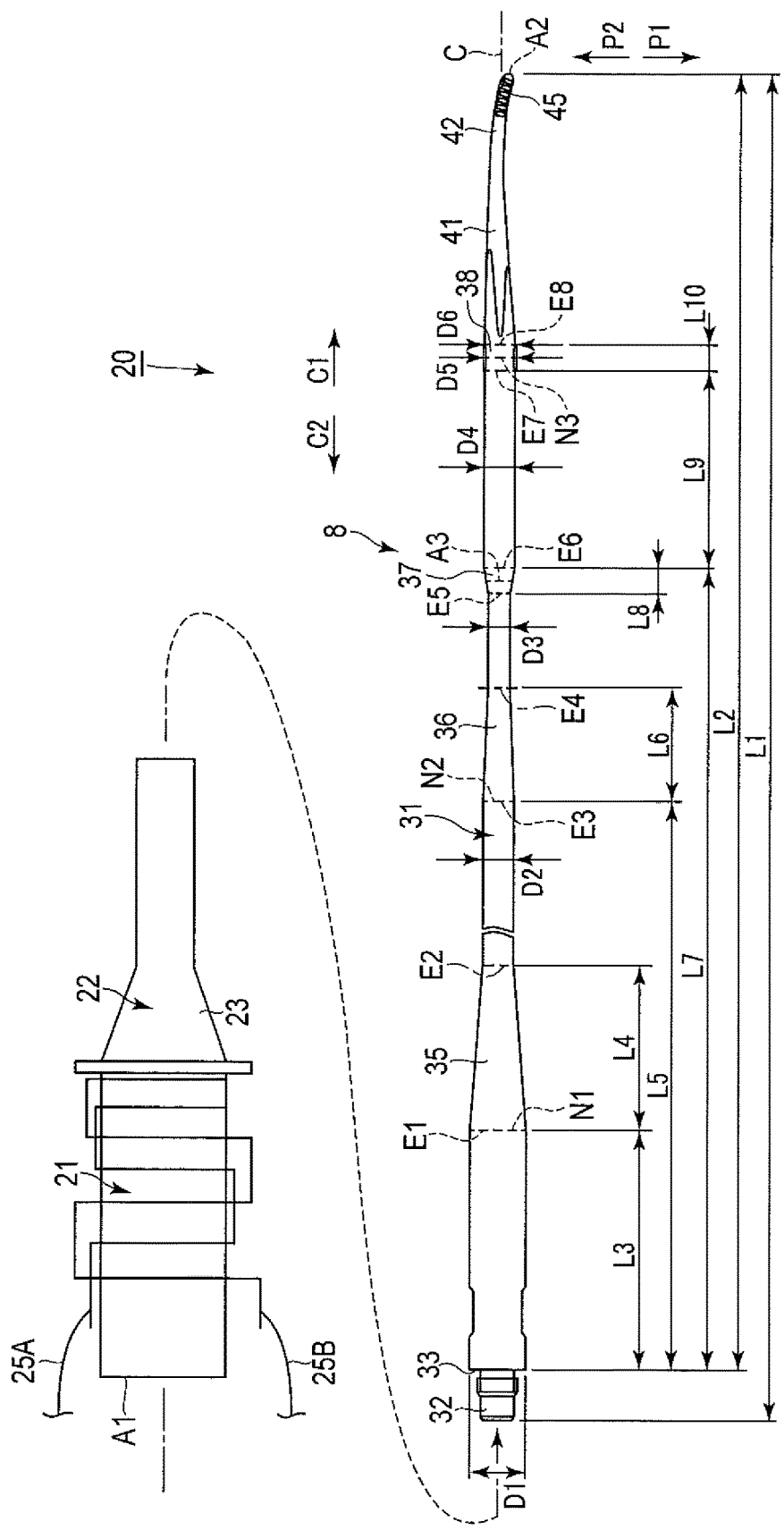
F I G. 2

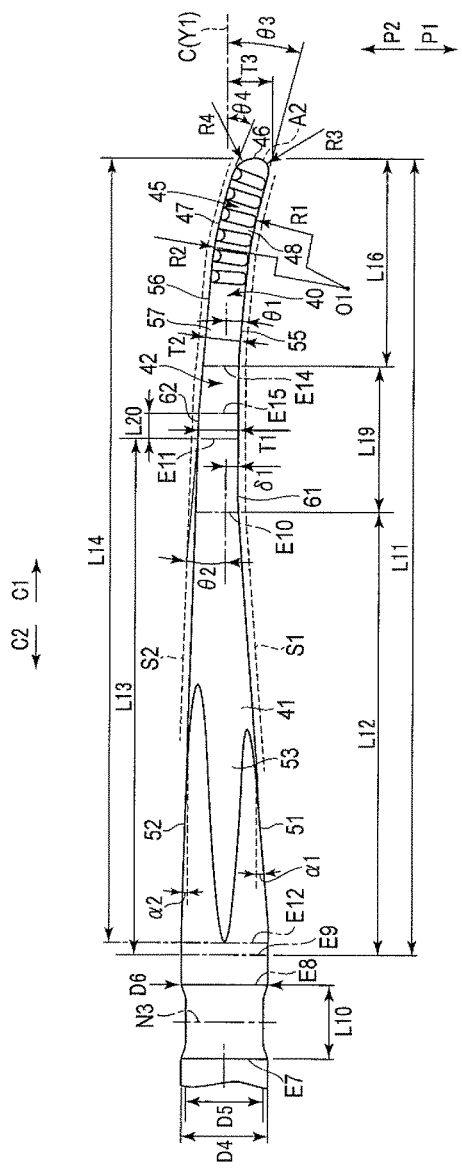
F I G. 3

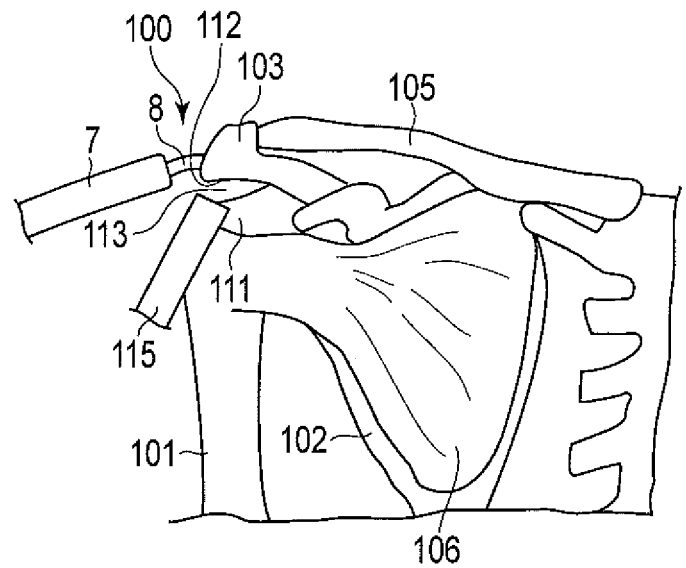
F I G. 7
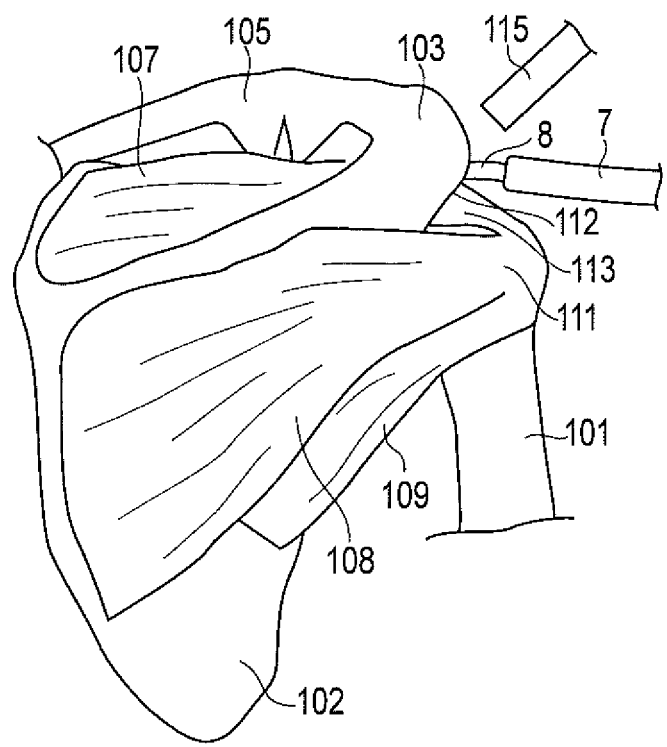
F I G. 8

ULTRASONIC PROBE AND ULTRASONIC INSTRUMENT

CROSS-REFERENCE TO RELATED APPLICATIONS

This is a Continuation Application of PCT Application No. PCT/JP2015/076188, filed Sep. 15, 2015 and based upon and claiming the benefit of priority from prior Japanese Patent Applications No. 2015-001840, filed Jan. 7, 2015, the entire contents of which are incorporated herein by reference.

BACKGROUND OF THE INVENTION

1. Field of the Invention

The present invention relates to an ultrasonic probe to perform cutting of, for example, a hard bone tissue and a cartilage tissue by ultrasonic vibration.

2. Description of the Related Art

In Jpn. Pat. Appln. KOKAI Publication No. 2005-152098, there is disclosed an ultrasonic treatment device including an ultrasonic probe (an ultrasonic horn). In this ultrasonic treatment device, an ultrasonic vibration generated in a vibration generating section (an ultrasonic vibration mechanism) is transmitted from a proximal side toward a distal side in the ultrasonic probe. In a distal portion of the ultrasonic probe, a scalpel portion is formed as a treating surface. In the scalpel portion, an outer surface of the ultrasonic probe is formed in an uneven state. The ultrasonic vibration is transmitted to the scalpel portion in a state where the scalpel portion is in contact with a treated target, whereby the treated target (e.g., a bone or another hard tissue) is cut.

BRIEF SUMMARY OF THE INVENTION

According to one aspect of the invention, an ultrasonic probe used in a shoulder joint, the ultrasonic probe being configured to transmit an ultrasonic vibration so as to treat the shoulder joint by use of the ultrasonic vibration, the ultrasonic probe including: a probe main body section which is extended along a longitudinal axis, and which is configured to transmit the ultrasonic vibration from a proximal side toward a distal side; a curved extending section which is provided on the distal side with respect to the probe main body section, and which is extended in a state of curving relative to the probe main body section toward a first intersecting direction side in a case where a certain direction intersecting the longitudinal axis is defined as the first intersecting direction; a first curved outer surface which faces the first intersecting direction side in the curved extending section; a second curved outer surface which faces a second intersecting direction side in the curved extending section in a case where an opposite direction of the first intersecting direction is defined as the second intersecting direction; a third curved outer surface which faces a first width direction side in the curved extending section in a case where two directions which intersect the longitudinal axis and are perpendicular to the first intersecting direction and the second intersecting direction are defined as a first width direction and a second width direction; a fourth curved outer surface which faces a second width direction side in the curved extending section; a first cutting surface which forms grooves on the second curved outer surface, and which is configured to cut a treated target, in projection from each of the first width direction and the second width direction, the first cutting surface being formed into a circular shape in which a center is positioned on the first intersecting direction side with respect to the curved extending section; a second cutting surface which is formed on the third curved outer surface, and which is configured to cut the treated target, the second cutting surface including first extending grooves extended along a thickness direction of the curved extending section; a third cutting surface which is formed on the fourth curved outer surface, and which is configured to cut the treated target, the third cutting surface including second extending grooves extended along the thickness direction of the curved extending section; and relay grooves which are extended on the first cutting surface, and in each of which one end is continuous with the first extending groove and the other end is continuous with the second extending groove.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic view of a vibrating body unit according to the first embodiment seen from a first width direction side;

FIG. 3 is a schematic view of a distal portion of an ultrasonic probe according to the first embodiment seen from the first width direction side;

FIG. 7 is a schematic view of a state where a bone is cut in a shoulder joint by use of an ultrasonic treatment device according to the first embodiment, which is seen from a front side of the shoulder joint;

FIG. 8 is a schematic view of a state where the bone is cut in the shoulder joint by use of the ultrasonic treatment device according to the first embodiment, which is seen from a rear side of the shoulder joint;

DETAILED DESCRIPTION OF THE INVENTION

First Embodiment

Figure 1:
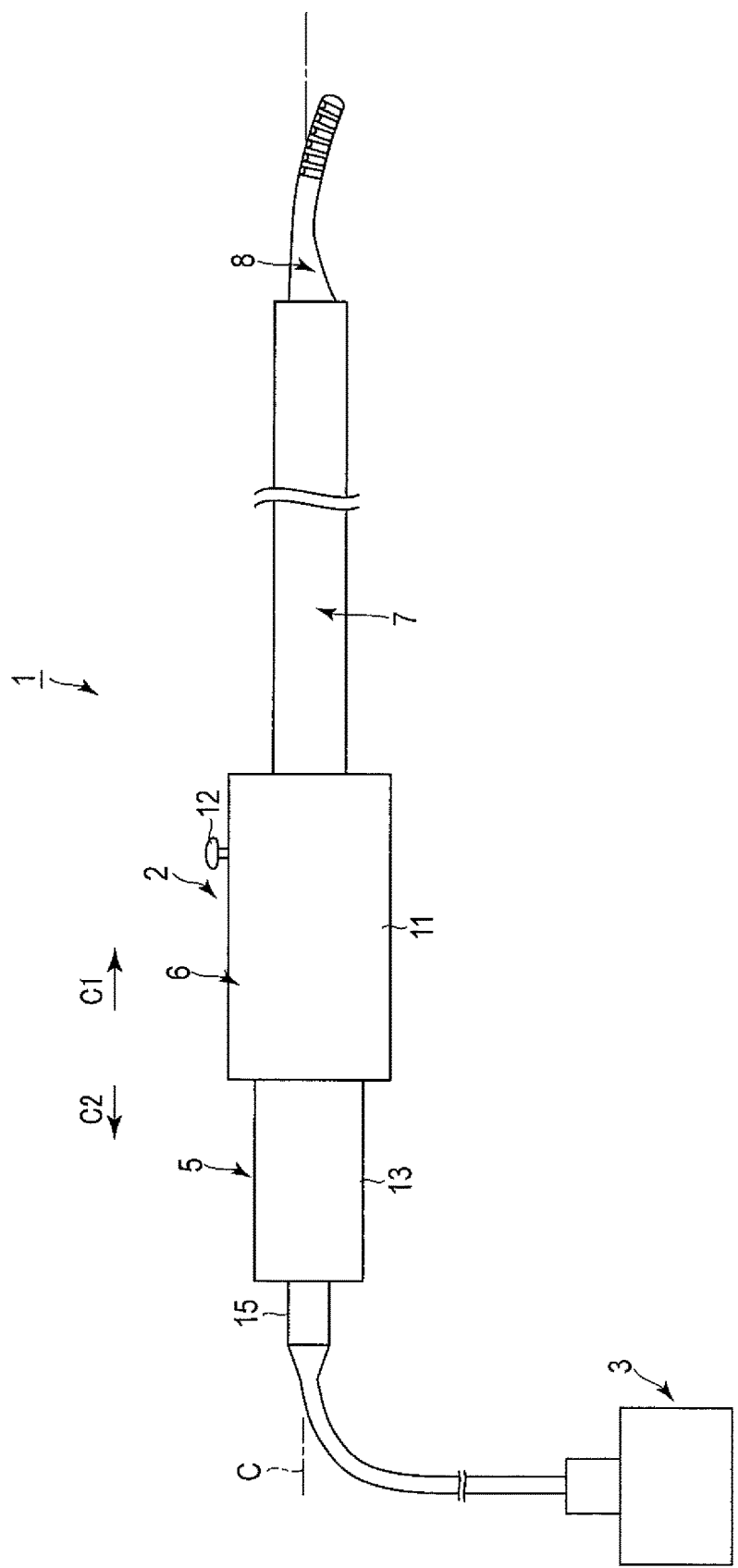
FIG. 1 is a view showing an ultrasonic treatment device according to a first embodiment of the present invention.

A first embodiment of the present invention will be described with reference to FIG. 1 to FIG. 11. FIG. 1 is a view showing an ultrasonic treatment system 1 of the present embodiment. As shown in FIG. 1, the ultrasonic treatment system 1 includes an ultrasonic treatment instrument (a hand piece) 2, an energy control device 3, and a transducer unit 5. The ultrasonic treatment instrument 2 has a longitudinal axis C. Here, a direction parallel to the longitudinal axis C is a longitudinal axis direction. One side of the longitudinal axis direction is a distal side (an arrow C1 side of FIG. 1), and a side opposite to the distal side is a proximal side (an arrow C2 side of FIG. 1).

The ultrasonic treatment tool 2 includes a holding unit 6, a sheath 7, and an ultrasonic probe 8. The holding unit 6 includes a holding casing 11 to be held by an operator, and an energy operating button 12 that is an energy operation input section attached to the holding casing 11 and configured to be operated by the operator. The sheath 7 that is a hollow tubular member extending along the longitudinal axis C is coupled with the distal side of the holding unit 6. The ultrasonic probe (a vibration transmitting member) 8 is inserted through the sheath 7. It is to be noted that a distal portion of the ultrasonic probe 8 projects from a distal end of the sheath 7 toward the distal side.

Furthermore, the transducer unit 5 having a transducer case 13 is coupled with the proximal side of the holding unit 6. The oscillator unit 5 is connected to one end of a cable 15. The other end of the cable 15 is connected to the energy control device 3. The energy control device 3 includes an electric power source, a conversion circuit to convert an electric power from the electric power source into a vibration generating electric power, a processor (a control section) including a CPU (central processing unit) or an ASIC (application specific integrated circuit), and a storage medium such as a memory. Inside the holding casing 11, there is disposed a switch (not shown) in which an ON/OFF state is changed by an input of an energy operation in the energy operating button 12. The switch is electrically connected to the processor of the energy control device 3 via a signal route extending through the vibrator unit 5 and an inside of the cable 15. Furthermore, in the ultrasonic treatment system 1, a vibrating body unit 20 extends through an inside of the holding casing 11 and an inside of the transducer case 13.

FIG. 2 is a view showing a constitution of the vibrating body unit 20. As shown in FIG. 2, the vibrating body unit 20 includes the ultrasonic probe 8 mentioned above, an ultrasonic transducer 21 that is a vibration generating section constituted of piezoelectric elements, and a relay transmitting member 22. The ultrasonic oscillator 21 and the relay transmitting member 22 are arranged in the oscillator case 13, and the relay transmitting member 22 is supported by the transducer case 13. The ultrasonic transducer 21 is attached to the relay transmitting member 22. Inside the holding casing 11, the ultrasonic probe 8 is connected to the distal side of the relay transmitting member 22. In the relay transmitting member 22, a sectional area changing portion 23 is disposed in which a sectional area perpendicular to the longitudinal axis C decreases toward the distal side. The sectional area changing portion (a horn portion) 23 is positioned on the distal side with respect to the ultrasonic transducer 21. The ultrasonic transducer 21 is connected to one end of each of electric wires 25A and 25B. The electric wires 25A and 25B extend through the inside of the cable 15, and the other end of the wire is connected to the energy control device 3.

The switch is switched to an ON state by the input of the energy operation in the energy operating button 12, whereby in the energy control device 3, the control section controls the conversion circuit, to supply the vibration generating electric power (a vibration generating current) to the ultrasonic vibrator 21 through the electric wires 25A and 25B. Consequently, in the ultrasonic transducer 21, an ultrasonic vibration occurs, and the generated ultrasonic vibration is transmitted to the ultrasonic probe 8 via the relay transmitting member 22. In this case, an amplitude of the ultrasonic vibration is enlarged in the sectional area changing portion 23 of the relay transmitting member 22.

The ultrasonic probe 8 includes a probe main body section 31 extending along the longitudinal axis C. The probe main body section 31 substantially linearly extends along the longitudinal axis C which is an axial center. On the proximal side of the probe main body section 31, an engagement connecting portion 32 is provided. The engagement connecting portion 32 is engaged in an engagement groove (not shown) disposed in the relay transmitting member 22 (e.g., by screwing an external thread into an internal thread), whereby the probe main body section 31 is connected to the distal side of the relay transmitting member 22. Thus, the relay transmitting member 22 is connected to the probe main body section 31, whereby an abutment surface 33 formed at a proximal end of the probe main body section 31 abuts on the relay transmitting member 22. The ultrasonic vibration is transmitted from the relay transmitting member 22 to the probe main body section 31 through the abutment surface 33.

Thus, the ultrasonic vibration is transmitted to the probe main body section 31, whereby in the probe main body section 31 (the ultrasonic probe 8), the ultrasonic vibration is transmitted from the proximal side toward the distal side. In a state where the ultrasonic vibration is transmitted through the probe main body section 31, the vibrating body unit 20 performs a longitudinal vibration in a vibrating direction parallel to the longitudinal axis direction in an established frequency range including an established frequency. In this case, a vibration antinode (the most proximal vibration antinode) A1 that is one of vibration antinodes of the longitudinal vibration is positioned at a proximal end of the vibrating body unit 20 (a proximal end of the relay transmitting member 22), and a vibration antinode (the most distal vibration antinode) A2 that is one of the vibration antinodes of the longitudinal vibration is positioned at a distal end of the vibrating body unit 20 (a distal end of the ultrasonic probe 8). Here, the vibration antinode A1 is positioned most proximally among the vibration antinodes of the longitudinal vibration, and the vibration antinode A2 is positioned most distally among the vibration antinodes of the longitudinal vibration. In a certain example, the vibrating body unit 20 is designed in a state of transmitting the ultrasonic vibration therethrough, thereby performing the longitudinal vibration at 47 kHz (the established frequency), and the vibrating body unit actually longitudinally vibrates in the frequency range (the established frequency range) of 46 kHz or more and 48 kHz or less.

The ultrasonic probe 8 has a total length L1 from its distal end to its proximal end (a proximal end of the engagement connecting portion 32) in the longitudinal axis direction. In the certain example, it is preferable that the total length L1 is 183.4 mm. Furthermore, the ultrasonic probe 8 has a longitudinal dimension L2 from the distal end to the abutment surface 33 (the proximal end of the probe main body section 31) in the longitudinal axis direction. In the certain example, it is preferable that the longitudinal dimension L2 is 177.5 mm.

In the probe main body section 31, a horn portion (a first horn portion) 33 is disposed. In the horn portion 35, the sectional area perpendicular to the longitudinal axis C decreases toward the distal side. The horn portion (a sectional area decreasing portion) 35 is positioned on the distal side with respect to the abutment surface 33, and the probe main body section 31 has a longitudinal dimension L3 from the abutment surface 33 to a proximal end (a vibration input end) E1 of the horn portion 35 in the longitudinal axis direction. In the certain example, it is preferable that the longitudinal dimension L3 is 29 mm. Furthermore, the horn portion (the first horn portion) 35 has a horn longitudinal dimension (a first horn longitudinal dimension) L4 from the proximal end (the vibration input end) E1 to a distal end (a vibration output end) E2 in the longitudinal axis direction. In the certain example, it is preferable that the horn longitudinal dimension L4 is 20 mm.

An outer diameter of the probe main body section 31 is kept to be substantially constant from the abutment surface 33 to the proximal end E1 of the horn portion 35 in the longitudinal axis direction. Therefore, the probe main body section 31 has an outer diameter D1 in the abutment surface 33 and at the proximal end E1 of the horn portion 35. In the certain example, it is preferable that the outer diameter D1 is 7 mm. Furthermore, in the horn portion 35, a sectional area decreases toward the distal side, and hence at the distal end E2 of the horn portion 35, the probe main body section 31 has an outer diameter D2 smaller than the outer diameter D1. That is, in the horn portion 35, the outer diameter of the probe main body section 31 decreases from the outer diameter D1 to the outer diameter D2 toward the distal side. In the certain example, it is preferable that the outer diameter D2 is 3.8 mm.

In a state where the vibrating body unit 20 longitudinally vibrates in the predetermined frequency range (e.g., 46 kHz or more and 48 kHz or less), a vibration node N1 that is one of vibration nodes of the longitudinal vibration is positioned at the proximal end E1 of the horn portion 35 or in the vicinity of the proximal end E1, and each of the vibration antinodes of the longitudinal vibration is positioned away from the horn portion 35 in the longitudinal axis direction. Consequently, in the horn portion 35 in which the sectional area decreases toward the distal side, the amplitude of the longitudinal vibration (the ultrasonic vibration) is enlarged. In the certain example, the longitudinal vibration in which the amplitude at the vibration antinode is 18 μm is transmitted to the proximal end E1 of the horn portion 35, and the amplitude of the longitudinal vibration in the horn portion 35 is enlarged. It is to be noted that in a state where the vibrating body unit 20 longitudinally vibrates at the predetermined frequency (e.g., 47 kHz) included in the predetermined frequency range, the vibration node N1 is positioned at the proximal end E1 of the horn portion 35.

In the probe main body section 31, a horn portion (a second horn portion) 36 is provided. In the horn portion 36, the sectional area perpendicular to the longitudinal axis C decreases toward the distal side. The horn portion (a sectional area decreasing portion) 36 is positioned on the distal side from the horn portion (the first horn portion) 35, and the probe main body section 31 has a longitudinal dimension L5 from the abutment surface 33 to a proximal end (a vibration input end) E3 of the horn portion 36 in the longitudinal axis direction. In the certain example, it is preferable that the longitudinal dimension L5 is 88.1 mm. Furthermore, the horn portion (the second horn portion) 36 has a horn longitudinal dimension (a second horn longitudinal dimension) L6 from the proximal end (the vibration input end) E3 to a distal end (a vibration output end) E4 in the longitudinal axis direction. In the certain example, it is preferable that the horn longitudinal dimension L6 is 14 mm.

In the probe main body section 31, the outer diameter is kept to be substantially constant from the distal end E2 of the horn portion (the first horn portion) 35 to the proximal end E3 of the horn portion (the second horn portion) 36 in the longitudinal axis direction. Therefore, the probe main body section 31 has the outer diameter D2 at the proximal end E3 of the horn portion 36. That is, at the distal end E2 of the horn portion 35 and the proximal end E3 of the horn portion 36, the outer diameter of the probe main body section 31 becomes the outer diameter D2 and has about the same size. Furthermore, in the horn portion 36, the sectional area decreases toward the distal side, and hence at the distal end E4 of the horn portion 36, the probe main body section 31 has an outer diameter D3 that is smaller than the outer diameter D2. That is, in the horn portion 36, the outer diameter of the probe main body section 31 decreases from the outer diameter D2 to the outer diameter D3 toward the distal side. In the certain example, it is preferable that the outer diameter 133 is 2.7 mm.

In the state where the vibrating body unit 20 longitudinally vibrates in the established frequency range (e.g., 46 kHz or more and 48 kHz or less), a vibration node N2 that is one of the vibration nodes of the longitudinal vibration is positioned at the proximal end E3 of the horn portion 36 or in the vicinity of the proximal end E3, and each of the vibration antinodes of the longitudinal vibration is positioned away from the horn portion 36 in the longitudinal axis direction. Consequently, in the horn portion 36 in which the sectional area decreases toward the distal side, the amplitude of the longitudinal vibration (the ultrasonic vibration) is enlarged. It is to be noted that in the state where the vibrating body unit 20 longitudinally vibrates at the established frequency (e.g., 47 kHz) included in the established frequency range, the vibration node N2 is positioned at the proximal end E3 of the horn portion 36. Furthermore, in the state where the vibrating body unit 20 longitudinally vibrates in the predetermined frequency range, the vibration node N2 is positioned on the distal side with respect to the vibration node N1.

In the probe main body section 31, a sectional area increasing portion 37 is provided. In the sectional area increasing portion 37, the sectional area perpendicular to the longitudinal axis C increases toward the distal side. The sectional area increasing portion 37 is positioned on the distal side with respect to the horn portion (the second horn portion) 36, and the probe main body section 31 has a longitudinal dimension L7 from the abutment surface 33 to a distal end (a vibration output end) E6 of the sectional area increasing portion 37 in the longitudinal axis direction. In the certain example, it is preferable that the longitudinal dimension L7 is 116.7 mm. Furthermore, the sectional area increasing portion 37 has an extending dimension L8 from a proximal end (a vibration input end) E5 to the distal end (the vibration output end) E6 in the longitudinal axis direction. The extending dimension L8 is small, and hence in the sectional area increasing portion 37, a distance from the proximal end E5 to the distal end E6 decreases.

In the probe main body section 31, the outer diameter is kept to be substantially constant from the distal end E4 of the horn portion (the second horn portion) 36 to the proximal end E5 of the sectional area increasing portion 37 in the longitudinal axis direction. Therefore, the probe main body section 31 has the outer diameter D3 at the proximal end E5 of the sectional area increasing portion 37. That is, at the distal end E4 of the horn portion 36 and the proximal end E5 of the sectional area increasing portion 37, the outer diameter of the probe main body section 31 becomes the outer diameter D3 and has about the same size. Furthermore, in the sectional area increasing portion 37, the sectional area increases toward the distal side, and hence at the distal end E6 of the sectional area increasing portion 37, the probe main body section 31 has an outer diameter D4 that is larger than the outer diameter D3. That is, in the sectional area increasing portion 37, the outer diameter of the probe main body section 31 increases from the outer diameter D3 to the outer diameter D4 toward the distal side. In the certain example, the outer diameter D4 is about the same as the outer diameter D2 at the proximal end E3 of the horn portion 36. In this case, it is preferable that the outer diameter D4 is 3.8 mm.

In the state where the vibrating body unit 20 longitudinally vibrates in the established frequency range, a vibration antinode A3 that is one of the vibration antinodes of the longitudinal vibration is positioned in the sectional area increasing portion 37. The vibration antinode A3 at which stress due to the ultrasonic vibration becomes zero is positioned in the sectional area increasing portion 37, and hence, also in the sectional area increasing portion 37 in which the sectional area increases toward the distal side, the amplitude of the longitudinal vibration (the ultrasonic vibration) hardly decreases. It is to be noted that in the state where the vibrating body unit 20 longitudinally vibrates in the established frequency range, the vibration antinode A3 is positioned on the distal side with respect to the vibration node N2, and in the present embodiment, the vibration antinode A3 is positioned second distally among the vibration antinodes of the longitudinal vibration.

The probe main body section 31 includes a supported portion 38 to be supported by the sheath 7 via an elastic member (not shown). The supported portion 38 is positioned on the distal side with respect to the sectional area increasing portion 37. The probe main body section 31 has a longitudinal dimension L9 from the distal end E6 of the sectional area increasing portion 37 to a proximal end E7 of the supported portion 38 in the longitudinal axis direction. In the certain example, it is preferable that the longitudinal dimension L9 is 24.1 mm. Furthermore, the supported portion 38 has an extending dimension L10 from the proximal end E7 to a distal end E8 in the longitudinal axis direction. The extending dimension L10 is small, and in the certain example, the extending dimension L10 is 3 mm.

In the probe main body section 31, the outer diameter is kept to be substantially constant from the distal end E6 of the sectional area increasing portion 37 to the proximal end E7 of the supported portion 38 in the longitudinal axis direction. Therefore, the probe main body section 31 has the outer diameter D4 at the proximal end E7 of the supported portion 38. That is, at the distal end E6 of the sectional area increasing portion 37 and the proximal end E7 of the supported portion 38, the outer diameter of the probe main body section 31 becomes the outer diameter D4 and has about the same size. In a proximal portion of the supported portion 38, the outer diameter of the probe main body section 31 decreases from the outer diameter D4 to an outer diameter D5. In the certain example, the outer diameter D5 is about 0.4 mm smaller than the outer diameter D4. In the supported portion 38, the outer diameter of the probe main body section 31 is kept to be substantially constant at the outer diameter D5 along a large part in the longitudinal axis direction. Further, in the distal portion of the supported portion 38, the outer diameter of the probe main body section 31 increases from the outer diameter D5 to an outer diameter D6. In consequence, the probe main body section 31 has the outer diameter D6 at the distal end E8 of the supported portion 38. The outer diameter D6 at the distal end E8 of the supported portion 38 is about the same as the outer diameter D4 at the proximal end E7 of the supported portion 38. Consequently, at the proximal end E7 and the distal end E8 of the supported portion 38, the sectional area of the probe main body section 31 which is perpendicular to the longitudinal axis C becomes about the same. In the certain example, it is preferable that the outer diameter D6 is 3.8 mm.

In the state where the vibrating body unit 20 longitudinally vibrates in the established frequency range, a vibration node N3 that is one of the vibration nodes of the longitudinal vibration is positioned in the supported portion 38. Consequently, the probe main body section 31 (the ultrasonic probe 8), which longitudinally vibrates, is also attached to the sheath 7 via the elastic member in the supported portion 38. Furthermore, the probe main body section is supported by the sheath 7 at the vibration node N3 of the longitudinal vibration, and hence in the state where the vibrating body unit 20 longitudinally vibrates in the predetermined frequency range, transmission of the ultrasonic vibration from the supported portion 38 to the sheath 7 is prevented. In the state where the vibrating body unit 20 longitudinally vibrates in the established frequency range, the vibration node (the most distal vibration node) N3 is positioned on the distal side with respect to the vibration node N2, and is positioned most distally among the vibration nodes of the longitudinal vibration. Furthermore, at the proximal end E7 and the distal end E8 of the supported portion 38, the sectional area of the probe main body section 31 which is perpendicular to the longitudinal axis C becomes about the same, and hence in the supported portion 38, the amplitude of the longitudinal vibration hardly changes.

Furthermore, the distal end of the sheath 7 is positioned on the distal side from the distal end E8 of the supported portion 38. Therefore, in the state where the vibrating body unit 20 longitudinally vibrates in the established frequency range, the vibration node N3 positioned most distally among the vibration nodes is positioned inside the sheath 7.

Figure 4:
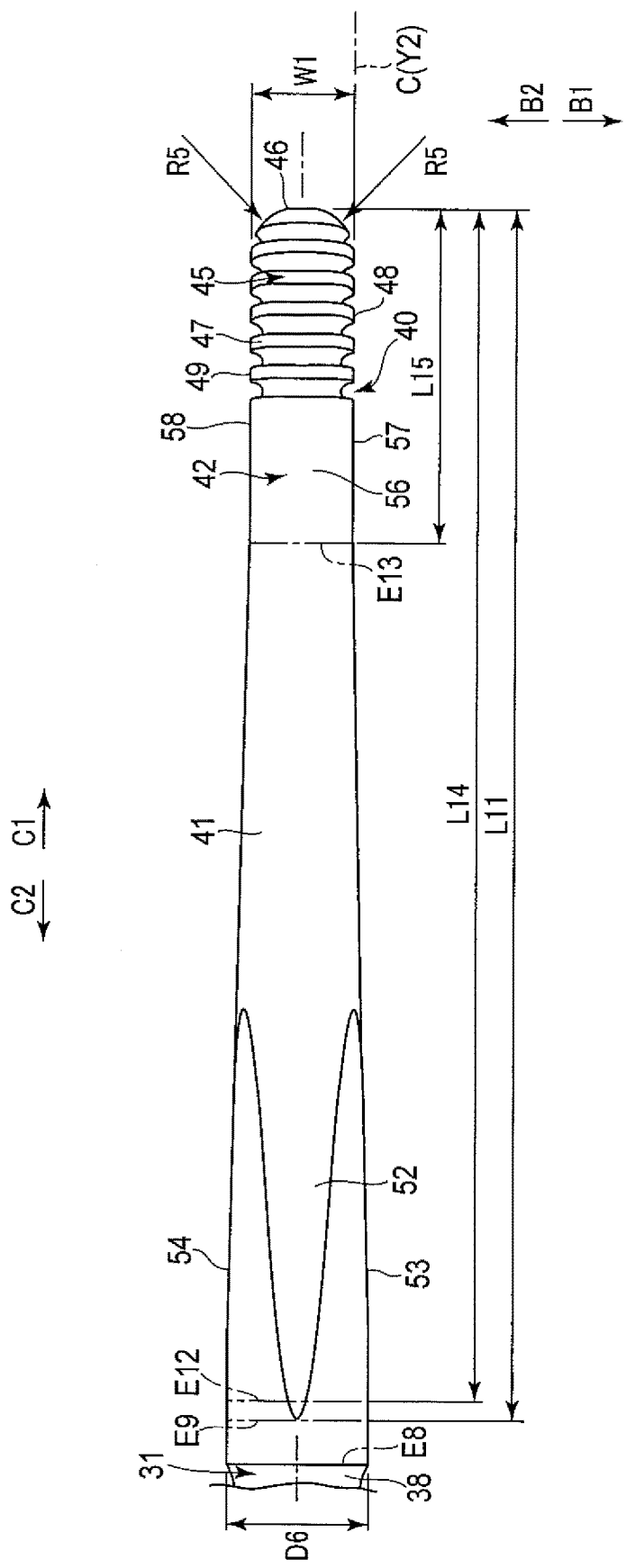
FIG. 4 is a schematic view of the distal portion of the ultrasonic probe according to the first embodiment seen from a second intersecting direction side.

FIG. 3 and FIG. 4 are views showing a constitution of the distal portion of the ultrasonic probe 8. Here, a certain direction that intersects (is substantially perpendicular to) the longitudinal axis C is a first intersecting direction (a direction of an arrow P1 in each of FIG. 2 and FIG. 3), and an opposite direction to the first intersecting direction (a first vertical direction) is a second intersecting direction (a direction of an arrow P2 in each of FIG. 2 and FIG. 3). Furthermore, one of two directions which intersect the longitudinal axis C (substantially perpendicularly) and are perpendicular to (intersect) the first intersecting direction (the first perpendicular direction) and the second intersecting direction (a second perpendicular direction) is a first width direction (a direction of an arrow B1 in FIG. 4). Further, an opposite direction to the first width direction is a second width direction (a direction of an arrow B2 in FIG. 4). Here, FIG. 2 and FIG. 3 are views of the ultrasonic probe 8 seen from a first width direction side, and FIG. 4 is a view of the ultrasonic probe 8 seen from a second perpendicular direction side. It is to be noted that in FIG. 3, a range shown by a broken line S1 and a broken line S2 projects from the distal end of the sheath 7 toward the distal side.

As shown in FIG. 3 and FIG. 4, the probe main body section 31 extends to a position located on the distal side with respect to the supported portion 38. That is, a distal end E9 of the probe main body section 31 is positioned on the distal side from the distal end E8 of the supported portion 38. However, a distance between the distal end E8 of the supported portion 38 and the distal end E9 of the probe main body section 31 in the longitudinal axis direction is small, and is about 1.2 mm in the certain example.

As described above, in the probe main body section 31, the amplitude of the longitudinal vibration is enlarged in the horn portion (the first horn portion) 35 and the horn portion (the second horn portion) 36, and the amplitude of the longitudinal vibration hardly changes in the sectional area increasing portion 37 and the supported portion 38. Due to the above-mentioned constitution, in the certain example, the longitudinal vibration of an amplitude of 80 µm occurs at the distal end E9 of the probe main body section 31, in a case where the longitudinal vibration of an amplitude of 18 µm at the vibration antinode is transmitted to the proximal end (the abutment surface 33) of the probe main body section 31.

A tapered section (a sectional area decreasing portion) 41 is continuous on the distal side of the probe main body section 31. In the tapered section (a third horn portion) 41, a sectional area perpendicular to a longitudinal axis C decreases toward the distal side. A proximal end of the tapered section 41 is continuous with the distal end E9 of the probe main body section 31. Therefore, the distal end E9 of the probe main body section 31 becomes a boundary position between the probe main body section 31 and the tapered section 41. The ultrasonic probe 8 has a longitudinal dimension L11 from the distal end to the proximal end (E9) of the tapered section 41 in the longitudinal axis direction. In the certain example, it is preferable that the longitudinal dimension L11 is 32.5 mm.

The tapered section 41 includes a first narrowed outer surface 51 facing a first intersecting direction side. In the tapered section 41, a distance (a first distance) δ from the longitudinal axis C to the first narrowed outer surface 51 in a first intersecting direction decreases from a proximal side toward the distal side, between the proximal end (E9) and a first narrowing end position (a first distance decreasing end position) E10 in the longitudinal axis direction. The first narrowing end position E10 is positioned on the distal side with respect to the proximal end (E9) of the tapered section 41. Consequently, the tapered section 41 has a first narrowing dimension (a first distance decreasing dimension) L12 between the proximal end (E9) and the first constricting end position E10 in the longitudinal axis direction. In the certain example, it is preferable that the first narrowing dimension L12 is 18 mm. In the present embodiment, the proximal end (E9) of the tapered section 41 becomes a proximal end of the first narrowed outer surface 51, and the first narrowing end position E10 becomes a distal end of the first narrowed outer surface 51.

Furthermore, the tapered section 41 includes a second narrowed outer surface 52 facing the second intersecting direction side. On the tapered section 41, a distance (a second distance) δ' from the longitudinal axis C to the second narrowed outer surface 52 in a second intersecting direction decreases from the proximal side toward the distal side, between the proximal end (E9) and a second narrowing end position (a second distance decreasing end position) E11 in the longitudinal axis direction. The second narrowing end position E11 is positioned on the distal side with respect to the first narrowing end position E10. Consequently, the tapered section 41 has a second narrowing dimension (a second distancing decrease dimension) L13 that is larger than the first narrowing dimension L12, between the proximal end (E9) and the second narrowing end position E11 in the longitudinal axis direction. In the certain example, it is preferable that the second constricting dimension L13 is 21 mm. In the present embodiment, the proximal end (E9) of the tapered section 41 becomes a proximal end of the second narrowed outer surface 52, and the second narrowing end position E11 becomes a distal end of the second constricted outer surface 52. Consequently, in the tapered section 41, the distal end of the first constricted outer surface 51 (the first constricting end position E10) is positioned on a proximal side as compared with the distal end of the second narrowed outer surface 52 (the second narrowing end position E11), and the distal end of the first narrowed outer surface 51 is disposed away from the distal end of the second narrowed outer surface 52 in the longitudinal axis direction.

Due to the above-mentioned constitution, in the tapered section 41, a thickness (a dimension) T of the ultrasonic probe 8 in the first intersecting direction and the second intersecting direction decreases toward the distal side, between the proximal end (E9) and the second narrowing end position E11 in the longitudinal axis direction. Therefore, the proximal end (E9) of the tapered section 41 becomes a thickness decreasing start position, and the second narrowing end position E11 becomes a thickness decreasing end position. Furthermore, in projection from a first width direction (one side of a width direction), a first narrowing angle α1 that is a narrowing angle (an acute angle) of the first narrowed outer surface 51 relative to the longitudinal axis direction is larger than a second narrowing angle α2 that is a narrowing angle (an acute angle) of the second narrowed outer surface 52 relative to the longitudinal axis direction, and the first narrowing angle is different from the second narrowing angle α2.

Furthermore, the tapered section 41 includes a third narrowed outer surface 53 directed in the first width direction, and a fourth narrowed outer surface 54 facing a second width direction. In the tapered section 41, between a width decreasing start position E12 and a width decreasing end position E13 in the longitudinal axis direction, a distance from the longitudinal axis C to the third narrowed outer surface 53 in the first width direction and a distance from the longitudinal axis C to the fourth narrowed outer surface 54 in the second width direction decrease from the proximal side toward the distal side. Consequently, in the tapered section 41, a width (a dimension) W of the ultrasonic probe 8 in the first width direction and the second width direction decreases toward the distal side, between the width decreasing start position E12 and the width decreasing end position E13 in the longitudinal axis direction. The ultrasonic probe 8 has a longitudinal dimension L14 from the distal end to the width decreasing start position E12 in the longitudinal axis direction. The longitudinal dimension L14 is smaller than the longitudinal dimension L11 from the distal end of the ultrasonic probe 8 to the proximal end (E9) of the tapered section 41 in the longitudinal axis direction. Therefore, the width decreasing start position E12 is positioned on the distal side with respect to the proximal end (E9) of the tapered section 41. However, the distance between the proximal end (E9) of the tapered section 41 and the width decreasing start position E12 in the longitudinal axis direction is small. In the certain example, it is preferable that the longitudinal dimension L14 is 32 mm. Further, in this example, the distance between the proximal end (E9) of the tapered section 41 and the width decreasing start position E12 in the longitudinal axis direction is about 0.5 mm. In the present embodiment, the width decreasing start position E12 becomes a proximal end of each of the third constricted outer surface 53 and the fourth constricted outer surface 54, and the width decreasing end position E13 becomes a distal end of each of the third narrowed outer surface 53 and the fourth narrowed outer surface 54.

The ultrasonic probe 8 has a longitudinal dimension L15 from the distal end to the width decreasing end position E13 in the longitudinal axis direction. In the present embodiment, the width decreasing end position E13 is positioned on the distal side with respect to the second narrowing end position E11. Further, the width decreasing end position E13 becomes a distal end of the tapered section 41. However, a distance between the second narrowing end position (the distal end of the second narrowed outer surface 52) E11 and the width decreasing end position E13 in the longitudinal axis direction is small. In the certain example, it is preferable that the longitudinal dimension L15 is 9 mm. Further, in this example, the distance between the second narrowing end position E11 and the width decreasing end position E13 in the longitudinal axis direction is about 2 mm.

The distance (the first distance) $\delta$ from the longitudinal axis C to the first narrowed outer surface 51 (an outer peripheral surface of the ultrasonic probe 8) in the first intersecting direction (a first perpendicular direction) decreases down to a distance $\delta_1$ between the proximal end (E9) of the tapered section 41 and the first narrowing end position E10 in the longitudinal axis direction. Therefore, at the first narrowing end position (the distal end of the first narrowed outer surface 51) E10, the ultrasonic probe 8 has the distance (the first distance) $\delta_1$ from the longitudinal axis C to the first narrowed outer surface 51 toward the first intersecting direction. The distance $\delta_1$ is smaller than a value of ½ of the outer diameter D6 at the distal end E9 of the probe main body section 31. In the certain example, the distance $\delta_1$ is 0.45 mm or more and 0.5 mm or less.

Between the proximal end (E9) of the tapered section 41 and the second narrowing end position E11 in the longitudinal axis direction, the thickness (the dimension) T of the ultrasonic probe 8 in the first intersecting direction and the second intersecting direction decreases down to a thickness T1. Therefore, at the second narrowing end position (the distal end of the second narrowed outer surface 52) E11, the ultrasonic probe 8 has the thickness T1 in the first intersecting direction (the first perpendicular direction) and the second intersecting direction (a second perpendicular direction). The thickness T1 is smaller than the outer diameter D6 at the distal end E9 of the probe main body section 31. In the certain example, it is preferable that the thickness T1 is 1.7 mm.

Between the width decreasing start position E12 and the width decreasing end position E13 in the longitudinal axis direction, the width (the dimension) W of the ultrasonic probe 8 in the first width direction and the second width direction decreases down to a width dimension W1. Therefore, at the width decreasing end position (the distal end of each of the third constricted outer surface 53 and the fourth constricted outer surface 54) E13, the ultrasonic probe 8 has the width dimension W1 in the first width direction and the second width direction. The width dimension W1 is smaller than the outer diameter D6 at the distal end E9 of the probe main body section 31. In the certain example, it is preferable that the width dimension W1 is 2.8 mm.

The tapered section 41 is constituted as described above, and hence in the tapered section 41, the sectional area perpendicular to the longitudinal axis C decreases toward the distal side. In the state where the vibrating body unit 20 longitudinally vibrates in the established frequency range (e.g., 46 kHz or more and 48 kHz or less), the vibration node (the most distal vibration node) N3 that is one of the vibration nodes of the longitudinal vibration is positioned in the supported portion 38, and is positioned in the vicinity of the proximal end (E9) of the tapered section 41. Further, in the state where the vibrating body unit 20 longitudinally vibrates in the predetermined frequency range, each of the vibration antinodes of the longitudinal vibration is positioned away from the tapered section 41 in the longitudinal axis direction. Consequently, in the tapered section 41 in which the sectional area decreases toward the distal side, the amplitude of the longitudinal vibration (ultrasonic vibration) is enlarged. In the certain example, in a case where the longitudinal vibration in which the amplitude in the tapered section 41 is 80 µm is transmitted, the amplitude of the longitudinal vibration at the distal end of the ultrasonic probe 8 is 140 µm or more and 150 µm or less.

Furthermore, in the present embodiment, a tapering dimension of the tapered section 41 from the proximal end (E9) to the distal end (E13) in the longitudinal axis direction is larger than a ⅛ wavelength ($\lambda/8$) in the state where the vibrating body unit 20 longitudinally vibrates in the established frequency range. That is, the ⅛ wavelength ($\lambda/8$) in the state where the vibrating body unit 20 longitudinally vibrates in the established frequency range is smaller than the tapering dimension of the tapered section 41 from the proximal end (E9) to the distal end (E13) in the longitudinal axis direction. In the certain example, in the state where the vibrating body unit 20 longitudinally vibrates at 46 kHz or more and 48 kHz or less (in the established frequency range), a ¼ wavelength ($\lambda/4$) from the vibration node (the most distal vibration node) N3 to the vibration antinode (the most distal vibration antinode) A2 is 34 mm or more and 35 mm or less. On the other hand, in this example, the tapering dimension of the tapered section 41 from the proximal end (E9) to the distal end (E13) in the longitudinal axis direction is about 23.5 mm, and is larger than the ⅛ wavelength in the state where the vibrating body unit 20 longitudinally vibrates at 46 kHz or more and 48 kHz or less (in the predetermined frequency range). Furthermore, in the tapered section 41, the first narrowing dimension L12 between the proximal end (E9) and the first narrowing end position E10 in the longitudinal axis direction is also 17.9 mm or more and 18 mm or less. Therefore, the first narrowing dimension L12 (i.e., the dimension of the first constricted outer surface 51 in the longitudinal axis direction) is also larger than the ⅛ wavelength in the state where the vibrating body unit 20 longitudinally vibrates at 46 kHz or more and 48 kHz or less (in the established frequency range). It is to be noted that the first narrowing end position E10 is positioned most proximally among the positions (e.g., E10, E11 and E13) at which the narrowing ends on an outer peripheral surface of the tapered section 41 (the narrowed outer surfaces 51 to 54).

In the ultrasonic probe 8, a curved extending section 40 is disposed on the distal side with respect to the tapered section 41 (and the probe main body section 31). The curved extending section 40 extends in a state of curving relative to the probe main body section 31 and the tapered section 41

(i.e., the longitudinal axis C) toward the first intersecting direction side. The curved extending section 40 includes a first curved outer surface 55 facing the first intersecting direction side (a side on which the curved extending section 40 curves), and a second curved outer surface 56 directed on the second intersecting direction side (a side opposite to the side on which the curve extending section 40 curves). Furthermore, the curved extending section 40 includes a third curved outer surface 57 facing the first width direction side, and a fourth curved outer surface 58 facing on a second width direction side. It is to be noted that by transmitting the ultrasonic vibration to the curved extending section 40 from the probe main body section 31 through the tapered section 41, the curved extending section 40 longitudinally vibrates together with the probe main body section 31 and the tapered section 41 in the established frequency range.

In projection from the first width direction (one side of the width direction), in the first curved outer surface 55 of the curved extending section 40, a region located on the distal side with respect to a first curve start position E14 curves relative to the longitudinal axis direction (the probe main body section 31) toward the first intersecting direction side. Furthermore, in the projection from the first width direction, in the second curved outer surface 56 of the curved extending section 40, a region located on the distal side with respect to a second curve start position E15 curves relative to the longitudinal axis direction toward the first intersecting direction side. That is, the first curved outer surface 55 starts curving relative to the longitudinal axis C in the first intersecting direction side at the first curve start position E14, and the second curved outer surface 56 starts curving relative to the longitudinal axis C toward the first intersecting direction side at the second curve start position E15. In the present embodiment, the first curve start position (a proximal end of the first curved outer surface 55) E14 is positioned on the distal side with respect to the second curve start position (a proximal end of the second curved outer surface 56) E15, and is positioned away from the second curve start position E15 in the longitudinal axis direction. Consequently, the curved extending section 40 extends toward the distal side from the second curve start position E15 which is the proximal end (a curve proximal end) thereof.

The ultrasonic probe 8 has a longitudinal dimension L16 from the distal end to the first curve start position E14 of the curved extending section 40 in the longitudinal axis direction. The longitudinal dimension L16 is smaller than the longitudinal dimension L15 from the distal end of the ultrasonic probe 8 to the width decreasing end position E13 in the longitudinal axis direction. Consequently, the first curve start position E14 of the curved extending section 40 is positioned on the distal side with respect to the width decreasing end position E13. In the certain example, the longitudinal dimension L16 is 8.5 mm.

Furthermore, in the ultrasonic probe 8, the second curve start position (the curve proximal end) E15 is positioned on the proximal side with respect to the first curve start position E14, and is positioned on the proximal side with respect to the width decreasing end position E13. Therefore, in the present embodiment, the proximal end (E15) of the curved extending section 40 is positioned on the proximal side with respect to the distal end (E13) of the tapered section 41. Consequently, in the present embodiment, a part of the tapered section 41 is formed by a part of the curved extending section 40. Here, in a certain example, a dimension between the second curve start position (the curve proximal end) E15 and the width decreasing end position E13 in the longitudinal axis direction is about 1 mm, and a dimension between the width decreasing end position E13 and the first curve start position E14 in the longitudinal axis direction is about 0.5 mm.

A first axis parallel outer surface 61 directed in the first intersecting direction is continuous between the first narrowed outer surface 51 and the first curved outer surface 55 in the longitudinal axis direction. The first axis parallel outer surface 61 extends in parallel (substantially parallel) with the longitudinal axis C between the first narrowing end position E10 and the first curve start position E14. Therefore, the first constricting end position E10 becomes a proximal end of the first axis parallel outer surface 61 and the first curve start position E14 becomes a distal end of the first axis parallel outer surface 61. Further, the first axis parallel outer surface 61 has an extending dimension (a first extending dimension) L19 in the longitudinal axis direction. On the first axis parallel outer surface 61, the distance δ from the longitudinal axis C toward the first intersecting direction is kept to be substantially constant at the distance δ1, from the first narrowing end position E10 to the first curve start position E14.

Furthermore, a second axis parallel outer surface 62 facing the second intersecting direction is continuous between the second narrowed outer surface 52 and the second curved outer surface 56 in the longitudinal axis direction. The second axis parallel outer surface 62 extends in parallel (substantially parallel) with the longitudinal axis C, between the second narrowing end position E11 and the second curve start position E15. Therefore, the second constricting end position E11 becomes a proximal end of the second axis parallel outer surface 62, and the second curve start position E15 becomes a distal end of the second axis parallel outer surface 62. Further, the second axis parallel outer surface 62 has an extending dimension (a second extending dimension) L20 in the longitudinal axis direction. The extending dimension L19 of the first axis parallel outer surface 61 is larger than the extending dimension L20 of the second axis parallel outer surface 62. On the second axis parallel outer surface 62, the distance δ' from the longitudinal axis C toward the second intersecting direction is kept to be substantially constant from the second narrowing end position E11 to the second curve start position E15.

Due to such a constitution as described above, between the second narrowing end position E11 and the second curve start position (the proximal end of the curved extending section 40) E15 in the longitudinal axis direction, the thickness T of the ultrasonic probe 8 in the first intersecting direction and the second intersecting direction is kept to be substantially constant at the thickness T1. Furthermore, between the width decreasing end position E13 and the distal end of the ultrasonic probe 8 in the longitudinal axis direction, the width W of the ultrasonic probe 8 in the first width direction and the second width direction is kept to be substantially constant at the width dimension W1.

Here, there is stipulated a reference plane (a first reference plane) Y1 passing along the longitudinal axis C and perpendicularly (substantially perpendicularly) to the first intersecting direction and the second intersecting direction. In the distal portion of the tapered section 41, the distance (the first distance) δ1 from the longitudinal axis C to the first axis parallel outer surface 61 (the outer peripheral surface of the ultrasonic probe 8) toward the first intersecting direction is smaller than a value of ½ of the thickness T1 of the ultrasonic probe 8 in the first intersecting direction and the second intersecting direction. Consequently, in the tapered section 41, the ultrasonic probe 8 is nonsymmetrical about the reference plane Y1 which is a central plane. Further, in the tapered section 41, a cross section gravity center in the cross section perpendicular to the longitudinal axis C shifts from the longitudinal axis C toward the second intersecting direction side. Especially, between the first narrowing end position E10 and the second curve start position (the curve proximal end) E15, there increases the shift of the cross section gravity center relative to the longitudinal axis C in the second intersecting direction side. Furthermore, there is stipulated a reference plane (a second reference plane) Y2 passing along the longitudinal axis C and perpendicularly (substantially perpendicularly) to the first width direction and the second width direction. In the tapered section 41, the ultrasonic probe 8 is substantially symmetric about the reference plane Y2 which is a central plane.

The curved extending section 40 includes a first curved extending section 42 that extends from the second curve start position E15 at the proximal end of the curved extending section 40 toward the distal side and curving relative to the probe main body section 31 and the tapered section 41 toward the first intersecting direction side. In the projection from the first width direction (one side of the width direction), in a region of an outer peripheral surface of the first curved extending section 42 which faces the first intersecting direction side, a tangent line at the first curve start position E14 has an acute angle $\theta 1$ relative to the longitudinal axis direction. Furthermore, in the projection from the first width direction, in a region of the outer peripheral surface of the first curved extending section 42 which is directed on the second intersecting direction side, a tangent line at the second curve start position (the curve proximal end) E15 has an acute angle $\theta 2$ relative to the longitudinal axis direction. The acute angle $\theta 1$ and the acute angle $\theta 2$ are larger than 0° and 10° or less. In the certain example, the acute angle $\theta 1$ is 5°, whereas the acute angle $\theta 2$ is 5°.

In the curved extending section 40, a second curved extending section 45 is continuous with the distal side of the first curved extending section 42. The second curved extending section 45 extends in a state of curving relative to the first curved extending section 42 toward the first intersecting direction side. In the projection from the first width direction (one side of the width direction), a region of an outer peripheral surface of the second curved extending section 45 which faces the first intersecting direction side extends in a circular shape of a curbing radius R1. Furthermore, in the projection from the first width direction, a region of the outer peripheral surface of the second curve extending section 45 which is directed on the second intersecting direction side extends in a circular shape of a curving radius R2.

A center O1 of each of the circle of the curving radius R1 and the circle of the curving radius R2 is positioned on the first intersecting direction side with respect to the curved extending section 40 (the ultrasonic probe 8). Consequently, in the projection from the first width direction (the second width direction), in a region of the outer peripheral surface of the second curved extending section 45 which faces the first intersecting direction side, an acute angle relative to the longitudinal axis direction increases toward the distal side. Similarly, in the projection from the first width direction (the second width direction), in a region of the outer peripheral surface of the second curved extending section 45 which is directed on the second intersecting direction side, an acute angle relative to the longitudinal axis direction increases toward the distal side. Therefore, in the second curved extending section 45, the acute angle relative to the longitudinal axis direction increases toward the distal side.

In the region of the outer peripheral surface of the second curved extending section 45 which faces the first intersecting direction side, a tangent line at a distal end has an acute angle $\theta 3$ relative to the longitudinal axis direction. Furthermore, in the region of the outer peripheral surface of the second curved extending section 45 which faces the second intersecting direction side, a tangent line at a distal end has an acute angle $\theta 4$ relative to the longitudinal axis direction. That is, at a distal end of the first curved outer surface 55, the curved extending section 40 has the acute angle $\theta 3$ relative to the longitudinal axis direction. Further, at a distal end of the second curved outer surface 56, the curved extending section 40 has the acute angle $\theta 4$ relative to the longitudinal axis direction. In the certain example, the curving radius R1 is 15 mm and the acute angle $\theta 3$ is 15°. Furthermore, the acute angle $\theta 4$ is stipulated in accordance with the curving radius R2. For example, in a case where the curving radius R2 is 16.5 mm, the acute angle $\theta 4$ is 20°. Further, in a case where the curving radius R2 is 30 mm, the acute angle $\theta 4$ is 15°. In the certain example, on the second curved outer surface 56 (the region of the outer peripheral surface of the second curved extending section 45 which faces the second intersecting direction side), the acute angle $\theta 4$ of the tangent line at the distal end relative to the longitudinal axis direction is 10° or more and 30° or less, and more preferably 20° or more and 25° or less.

Furthermore, a direction that is perpendicular (substantially perpendicular) to an extending direction and that is perpendicular (substantially perpendicular) to the width direction in the ultrasonic probe 8 is a thickness direction. In the curved extending section 40, the extending direction of the ultrasonic probe 8 is not parallel to the longitudinal axis, and hence in the curved extending section 40, the thickness direction is not parallel to the first intersecting direction and the second intersecting direction. The ultrasonic probe 8 is kept to be substantially constant at a thickness dimension T2 in the thickness direction from the first curve start position E14 to the distal end in the longitudinal axis direction. That is, between the first curve start position E14 and the distal end of the ultrasonic probe 8, the thickness dimension T2 that is a distance between the first curved outer surface 55 and the second curved outer surface 56 is kept to be substantially constant. In the certain example, the thickness dimension T2 is 1.5 mm. Therefore, the acute angles $\theta 1$ to $\theta 4$ and the curving radiuses R1 and R2 are determined in a state where the thickness dimension T2 of the ultrasonic probe 8 is substantially constant from the first curve start position E14 to the distal end.

Furthermore, the region of the outer peripheral surface of the second curved extending section 45 which faces the first intersecting direction side has a separation distance T3 from the longitudinal axis C toward the first intersecting direction at the distal end. In the certain example, it is preferable that the separation distance T3 is 1.9 mm.

The second curved extending section 45 includes a distal surface 46 that forms the distal end of the ultrasonic probe 8. In the projection from the first width direction (one side of the width direction), a portion between the first curved outer surface 55 (the region of the outer peripheral surface of the second curved extending section 45 which is directed on the first intersecting direction side) and the distal surface 46 is formed into a curved surface of a corner radius R3. Furthermore, in the projection from the first width direction, a portion between the second curved outer surface 56 (the region of the outer peripheral surface of the second curved extending section 45 which faces the second intersecting direction side) and the distal surface 46 is formed into a curved surface of a corner radius R4. In the certain example, the corner radius R3 is 0.5 mm and the corner radius R4 is 0.9 mm. Furthermore, in projection from the second intersecting direction (one side of the intersecting direction), there is formed into a curved surface of a corner radius R5 each of a portion between a third curved outer surface 57 (the region of the outer peripheral surface of the second curved extending section 45 which faces the first width direction side) and the distal surface 46 and a portion between a fourth curved outer surface 58 (the region of the outer peripheral surface of the second curved extending section 45 which is directed on the second width direction side) and the distal surface 46.

Figure 5:
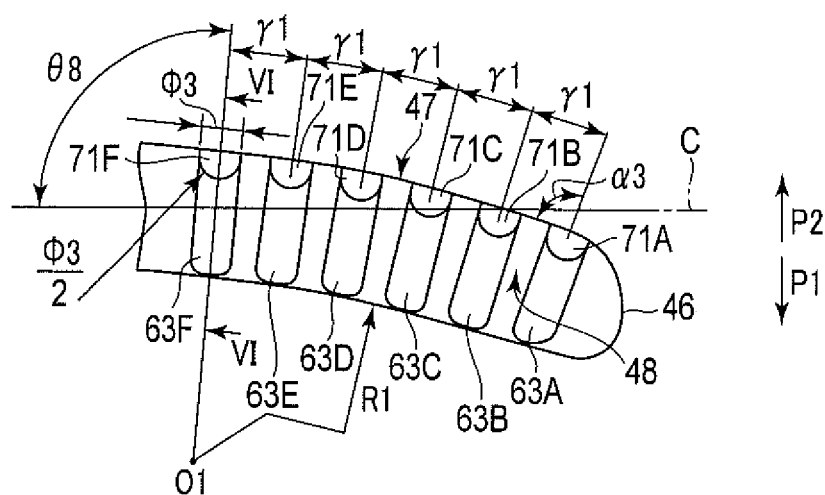
FIG. 5 is a schematic view of a second curved extending section according to the first embodiment seen from a first width direction side.
Figure 6:
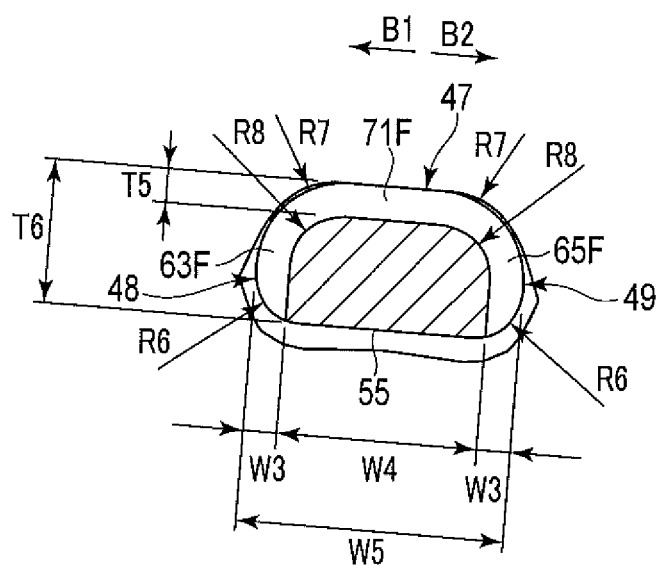
FIG. 6 is a cross-sectional view along the VI-VI line of FIG. 5.

FIG. 5 is a view of the second curved extending section 45 (a distal portion of the curved extending section 40) seen from the first width direction side. Further, FIG. 6 is a cross-sectional view along the VI-VI line of FIG. 15 and shows a cross section perpendicular to an extending direction of the curved extending section 40.

As shown in FIG. 3 to FIG. 6, cutting surfaces (treating surfaces) 47 to 49 are disposed in the second curved extending section 45. A first cutting surface 47 is disposed on the second curved outer surface 56 (a region of an outer surface of the curved extending section 40 which faces the second intersecting direction side). Further, a second cutting surface 48 is provided on the third curved outer surface 57 (a region of the outer surface of the curved extending section 40 which is directed on the first width direction side), and a third cutting surface 49 is disposed on the fourth curved outer surface 58 (a region of the outer surface of the curved extending section 40 which faces the second width direction side). After-mentioned grooves are formed in each of the abrading surfaces 47 to 49. Furthermore, each of the cutting surfaces 47 to 49 extends from a distal end (the distal surface 46) of the curved extending section 40 toward the proximal side. The first cutting surface 47 is provided in the second curved extending section 45 and on the second curved outer surface 56. Consequently, in the projection from each of the first width direction and the second width direction, the first abrading surface 47 is formed into a circular shape in which the center (O1) is positioned on the first intersecting direction side with respect to the curved extending section 40.

The second curved extending section 45 has a thickness dimension T6 between the first cutting surface 47 and the first curved outer surface 55 in the thickness direction of the curved extending section 40. The thickness dimension T6 between the first abrading surface 47 and the first curved outer surface 55 is about the same size as the thickness dimension T2. Furthermore, the second curved extending section 45 has a width dimension W5 between the second cutting surface 48 (the third curved outer surface 57) and the third cutting surface 49 (the fourth curved outer surface 58) in the first width direction and the second width direction. The width dimension W5 between the second abrading surface 48 and the third abrading surface 49 is about the same size as the width dimension W1. Consequently, in a range in which the first cutting surface 47 extends (the second curved extending section 45), the thickness dimension T6 (T2) between the first cutting surface 47 and the first curved outer surface 55 in the thickness direction of the curved extending section 40 is smaller than the width dimension W5 (W1) between the third curved outer surface 57 and the fourth curved outer surface 58 in the first width direction and the second width direction.

On the second cutting surface 48, a plurality of (six in the present embodiment) extending grooves (first extending grooves) 63A to 63F are formed, and on the third cutting surface 49, a plurality of (six in the present embodiment) extending grooves (second extending grooves) 65A to 65F are formed. Each of the extending grooves 63A to 63F extends substantially perpendicularly to the extending direction of the curved extending section 40, and extends along the thickness direction of the curved extending section 40 in the present embodiment. Furthermore, the extending grooves 63A to 63F are rowed in parallel in the extending direction of the curved extending section 40. Each of the extending grooves 63A to 63F has an acute angle γ1 between the extending groove and the extending groove (corresponding one or two of the grooves 63A to 63F) disposed adjacent in the extending direction of the curved extending section 40. That is, the extending direction of each of the extending grooves 63A to 63F shifts as much as the acute angle γ1 from the extending direction of the adjacent extending groove (corresponding one or two of the grooves 63A to 63F). Furthermore, there is stipulated the most proximal extending groove 63F positioned most proximally among the extending grooves 63A to 63F. The extending direction of the most proximal extending groove 63F has an obtuse angle θ8 relative to the proximal side. In the certain example, the acute angle γ1 is 3° and the obtuse angle θ8 is 95°.

The extending grooves (first extending grooves) 63A to 63F extend as described above, and hence in the projection from the first width direction, the extending grooves 63A to 63F are extended on the second cutting surface 48 perpendicularly to the circular first cutting surface 47 in which the center (O1) is positioned on the first intersecting direction side with respect to the curved extending section 40. Therefore, in the present embodiment, in the projection from the first width direction, each of the extending grooves 63A to 63F forms an angle α3 between the extending groove and the first cutting surface 47, and the angle α3 is 90°. Further, the extending grooves 63A to 63F intersect at the center (O1) of the circle of the first cutting surface 47. Each of the extending grooves 63A to 63F has a width φ3 and a depth W3. In the certain example, the width φ3 is 0.5 mm and the depth W3 is 0.35 mm.

Each of the extending grooves (the second extending grooves) 65A to 65F is substantially symmetric with the corresponding extending groove (corresponding one of the grooves 63A to 63F) about the reference plane Y2 which is the central plane. Consequently, in the projection from the second width direction, the extending grooves 65A to 65F are extended on the third cutting surface 49 perpendicularly to the circular first cutting surface 47 in which the center is positioned on the first intersecting direction side with respect to the curved extending section 40. Furthermore, the acute angle γ1, the obtuse angle θ8, the width φ3 and the depth W3 are stipulated in connection with the extending grooves 65A to 65F in the same manner as in the extending grooves 63A to 63F. Furthermore, the second curved extending section 45 has a width direction dimension W4 in the first width direction and the second width direction from a bottom position of each of the extending grooves 63A to 63F to a bottom position of the corresponding extending groove (corresponding one of the grooves 65A to 65F). In the certain example, the width direction dimension W4 is 2.1 mm or more and 2.15 mm or less.

Furthermore, a plurality of (six in the present embodiment) relay groves 71A to 71F are formed on the first cutting surface 47. Each of the relay groves 71A to 71F extends substantially perpendicularly to the extending direction of the curved extending section 40, and the respective grooves are extended along the width directions (the first width direction and the second width direction) of the curved extending section 40 in the present embodiment. One end of each of the relay groves 71A to 71F is continuous with the corresponding extending groove (corresponding one of the groves 63A to 63F), and the other end of each of the relay groves 71A to 71F is continuous with the corresponding extending groove (corresponding one of the grooves 65A to 65F). Each of the relay groves 71A to 71F has the same width θ3 as in the extending grooves 63A to 63F and 65A to 65F, and has a depth T5. In the certain example, the depth T5 is 0.3 mm or more and 0.35 mm or less. Furthermore, a bottom surface of each of the relay groves 71A to 71F seen from a second cutting surface 48 side (one side of the width direction) is formed into a circular shape of a radius φ3/2.

In the cross section of the second curved extending section 45 which is perpendicular to the extending direction, there is formed into a curved surface of a corner radius R6 each of a portion between the first curved outer surface 55 (a region of an outer surface which faces the first intersecting direction side) and the second cutting surface 48 and a portion between the first curved outer surface 55 and the third cutting surface 49. Furthermore, in the cross section of the second curved extending section 45 which is perpendicular to the extending direction, there is formed into a curved surface of a corner radius R7 each of a portion between the first cutting surface 47 and the second cutting surface 48 and a portion between the first cutting surface 47 and the third cutting surface 49.

The curved surface portion of the corner radius R6 is formed along the range S1 of FIG. 3 in the longitudinal axis direction, and the curved surface portion of the corner radius R7 is formed along the range S2 of FIG. 3 in the longitudinal axis direction. That is, the curved surface portion of the corner radius R6 and the curved surface portion of the corner radius R7 extend from the distal end of the ultrasonic probe 8 to the tapered section 41 in the longitudinal axis direction, and the curved surface portion of the corner radius R6 and the curved surface portion of the corner radius R7 are formed in a projecting portion (an exposed portion) of the ultrasonic probe 8 from the distal end of the sheath 7. Consequently, in a part of the tapered section 41 and the curved extending section 40, in the cross section perpendicular to the extending direction, there is formed into the curved surface of the corner radius R6 in each of a portion between a region of an outer surface which faces the first intersecting direction side and a region of an outer surface which faces the first width direction side and a portion between the region of the outer surface which faces the first intersecting direction side and a region of the outer surface which faces the second width direction side. Further, in the part of the tapered section 41 and the curved extending section 40, in the cross section perpendicular to the extending direction, there is formed into the curved surface of the corner radius R7 in each of a portion between a region of the outer surface which is directed on the second intersecting direction side and the region of the outer surface which is directed on the first width direction side and a portion between the region of the outer surface which is directed on the second intersecting direction side and the region of the outer surface which is directed on the second width direction side.

Also in the present embodiment, in the cross section of the second curved extending section 45 which is perpendicular to the extending direction, there is formed into a curved surface of a corner radius R8 in each of a portion between each of the relay groves 71A to 71F and the corresponding extending groove (corresponding one of the grooves 63A to 63F) and a portion between each of the relay groves 71A to 71F and the corresponding extending groove (corresponding one of the grooves 65A to 65F). In the certain example, the corner radius R8 is 0.55 mm.

Next, a function and an effect of the ultrasonic probe 8 of the present embodiment will be described. FIG. 7 and FIG. 8 are views showing a state where a bone is cut in a shoulder joint 100 by use of an ultrasonic treatment system 1. FIG. 7 is a view of the shoulder joint 100 seen from a front side (a chest side), and FIG. 8 is a view of the shoulder joint 100 seen from a rear side (a back side). As shown in FIG. 7 and FIG. 8, the shoulder joint 100 is a joint between a humerus 101 and a scapula 102. The scapula 102 includes an acromion 103. The acromion 103 is coupled with a clavicle 105. From the scapula 102, there origin a subscapularis muscle 106, a supraspinatus muscle 107, an infraspinatus muscle 108 and a teres minor muscle 109. On a lower side of the acromion 103, a rotator cuff 111 is formed as a tendon of the subscapularis muscle 106, the supraspinatus muscle 107, the infraspinatus muscle 108 and the teres minor muscle 109. The humerus 101 extends from the rotator cuff 111. Furthermore, a cavity 113 is formed between a lower surface 112 of the acromion 103 and the rotator cuff 111.

In the present embodiment, a distal portion of a rigid endoscope (an arthroscope) 115 and a distal portion of the ultrasonic probe 8 are inserted into the cavity 113 between the acromion 103 and the rotator cuff 111. Each of the rigid endoscope 115 and the ultrasonic probe 8 is inserted from the outside of a human body into the cavity 113 through one of an insertion area of the front side, an insertion area of a lateral side and an insertion area of the rear side. However, the insertion area of the rigid endoscope 115 is different from the insertion area of the ultrasonic probe 8. In FIG. 7 and FIG. 8, the rigid endoscope 115 is inserted into the cavity 113 from the insertion area of the front side, and the ultrasonic probe 8 is inserted into the cavity 113 through the insertion area of the lateral side. Further, in the cavity 113 under observation with the rigid endoscope 115, one of the cutting surfaces 47 to 49 of the ultrasonic probe 8 is brought into contact with the lower surface 112 of the acromion 103. The ultrasonic vibration is transmitted to the cutting surfaces 47 to 49 in a state where the one of the abrading surfaces 47 to 49 is in contact with the lower surface 112 of the acromion 103, whereby cutting of a bone spur (a bone) is performed in the lower surface 112 of the acromion 103. It is to be noted that the abrading of the bone spur in the lower surface 112 of the acromion 103 is performed in a state where the second curved extending section 45 is immersed in a liquid (physiological saline).

Figure 9:
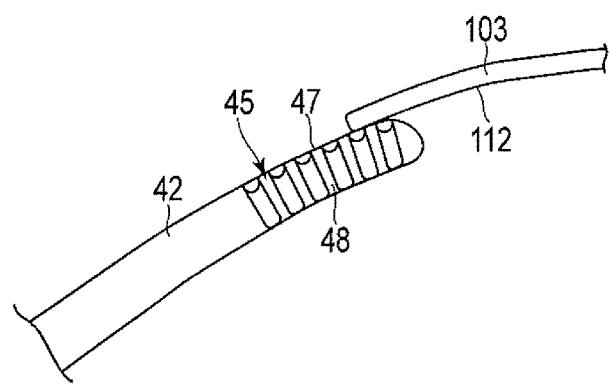
FIG. 9 is a schematic view showing a state where a first cutting surface of a curved extending section of the ultrasonic probe according to the first embodiment is in contact with a lower surface of an acromion.
Figure 10:
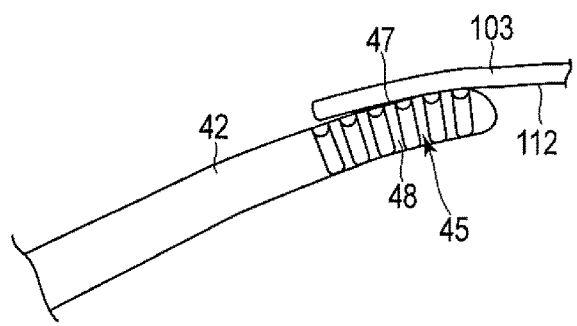
FIG. 10 is a schematic view showing a state where the first cutting surface of the curved extending section of the ultrasonic probe according to the first embodiment is in contact with a position different from that of FIG. 9 in the lower surface of the acromion.

FIG. 9 and FIG. 10 are views showing a state where the first cutting surface 47 of the second curved extending section 45 of the ultrasonic probe 8 is in contact with the lower surface 112 of the acromion 103. In FIG. 10, the first cutting surface 47 is brought into contact with a position different from that of FIG. 9 in the lower surface 112 of the acromion 103. Here, in the ultrasonic probe 8, the first curved extending section 42 curves toward a first perpendicular direction side relative to the probe main body section 31 extending along the longitudinal axis C, and the second curved extending section 45 curves further toward the first perpendicular direction side relative to the first curved extending section 42. Further, in the second curved extending section 45, an acute angle relative to the longitudinal axis direction increases toward the distal side, and in the second curved extending section 45 and the second curved outer surface 56, the first cutting surface 47 is disposed. Consequently, in the present embodiment, in the projection from each of the first width direction and the second width direction, the first cutting surface 47 is formed into the circular shape in which the center (O1) is positioned on the first intersecting direction side with respect to the curved extending section 40. The cavity 113 between the acromion 103 and the rotator cuff 111 is narrow, and the lower surface 112 of the acromion 103 is formed into a curved surface. The first curved extending section 42 and the second curved extending section 45 are formed as described above, so that the first cutting surface 47 can appropriately be brought into contact with the lower surface 112 of the acromion 103 which is formed into the curved surface.

For example, in FIG. 9 and FIG. 10, the positions which come in contact with the first cutting surface 47 are different from each other in the lower surface 112 of the acromion 103, and hence a contact angle of the first abrading surface 47 with the lower surface 112 of the acromion 103 varies. In the present embodiment, the first curved extending section 42 and the second curved extending section 45 are formed as described above, and hence even when the contact angle of the first cutting surface 47 with the lower surface 112 of the acromion 103 changes, it is possible to appropriately bring the first cutting surface 47 into contact with the lower surface 112 of the acromion 103. For example, in each of FIG. 9 and FIG. 10, the first cutting surface 47 appropriately comes in contact with the lower surface 112 of the acromion 103. That is, at any position of the lower surface 112 of the acromion 103 (i.e., even when the contact angle of the first cutting surface 47 with the lower surface 112 of the acromion 103 is any angle), the first cutting surface 47 can appropriately be brought into contact with the lower surface 112 of the acromion 103.

Furthermore, in the present embodiment, the first cutting surface 47 is provided on the second curved outer surface 56 of the curved extending section 40, and on the second curved outer surface 56 (a region of an outer peripheral surface of the curved extending section 40 which faces the second intersecting direction side), the acute angle θ4 of the tangent line at the distal end relative to the longitudinal axis direction is 10° or more and 30° or less (preferably 20° or more and 25° or less). By setting the acute angle θ4 to be 10° or more and 30° or less (especially 20° or more and 25° or less), the first cutting surface 47 has a shape corresponding to the lower surface 112 of the acromion 103, and at any position of the lower surface 112 of the acromion 103, the first cutting surface 47 can further easily and appropriately be brought into contact with the lower surface 112 of the acromion 103.

Furthermore, on the first cutting surface 47, the relay grooves 71A to 71F extend substantially perpendicularly to the extending direction of the curved extending section 40 (i.e., the vibrating direction of the longitudinal vibration). The relay grooves 71A to 71F extend substantially perpendicularly to the vibrating direction of the longitudinal vibration, and hence by longitudinally vibrating the second curved extending section 45 by the ultrasonic vibration in a state where the first cutting surface 47 is in contact with the section, the bone (the bone spur) is appropriately cut. That is, it is possible to appropriately cut the hard bone.

As described above, in the present embodiment, also in a joint cavity such as a cavity 113 between an acromion 103 and a rotator cuff 111, i.e., a narrow space, a first cutting surface 47 is easy to come in contact with a hard tissue, and the hard tissue is appropriately cut with the first cutting surface 47. That is, also in the narrow space, it is possible to acquire an accessibility to the hard tissue and cutting properties of the hard tissue.

In the present embodiment, the bone may be cut by bringing the second cutting surface 48 or the third cutting surface 49 into contact with the lower surface 112 of the acromion 103. Furthermore, in a case where the first cutting surface 47 is brought into contact with the lower surface 112 of the acromion 103 to cut the bone (the bone spur), the bone is cut by the second cutting surface 48 and the third cutting surface 49 in the vicinity of an area to be cut by the first cutting surface 47. Thus, the bone is cut by the cutting surface 48 or 49, thereby preventing only the area cut by the first cutting surface 47 from being concaved and preventing a stepped area from being formed on the lower surface 112 of the acromion 103.

Furthermore, the extending grooves 63A to 63F of the second cutting surface 48 and the extending grooves 65A to 65F of the third cutting surface 49 extend substantially perpendicularly (along the thickness direction of the curved extending section 40) to the extending direction of the ultrasonic probe 8 (i.e., the vibrating direction by the longitudinal vibration). The extending grooves (the first extending grooves) 63A to 63F extend substantially perpendicularly to the vibrating direction by the longitudinal vibration, and hence the cutting properties of the bone improve in a case where the bone is cut with the second cutting surface 48 by use of the ultrasonic vibration. Similarly, the extending grooves (the second extending grooves) 65A to 65F extend substantially perpendicularly to the vibrating direction by the longitudinal vibration, and hence the cutting properties of the bone improve in a case where the bone is cut with the third cutting surface 49 by use of the ultrasonic vibration.

Furthermore, the extending grooves (the first extending grooves) 63A to 63F are extended perpendicularly to the circular first cutting surface 47 on the second cutting surface 48, and the extending grooves (the second extending grooves) 65A to 65F are extended perpendicularly to the circular first cutting surface 47 on the third cutting surface 49. Consequently, when the bone is cut with the second cutting surface 48 or the third cutting surface 49, the cutting properties of the bone improve.

Furthermore, each of the relay groves 71A to 71F is continuous with the corresponding extending groove (corresponding one of the grooves 63A to 63F) and the corresponding extending groove (corresponding one of the grooves 65A to 65F). Consequently, when the bone is cut with the cutting surfaces 47 to 49, the bone is evenly and uniformly cut, and the cutting properties further improve.

Furthermore, in the present embodiment, there is formed into the curved surface of the corner radius R8 in each of the portion between each of the relay groves 71A to 71F and the corresponding extending groove (corresponding one of the grooves 63A to 63F) and the portion between each of the relay groves 71A to 71F and the corresponding extending groove (corresponding one of the grooves 65A to 65F). Consequently, the bone is effectively prevented from being left uncut between each of the relay groves 71A to 71F and the corresponding extending groove (corresponding one of the grooves 63A to 63F) and between each of the relay groves 71A to 71F and the corresponding extending groove (corresponding one of the grooves 65A to 65F).

Furthermore, in the present embodiment, the distal end of the first narrowed outer surface 51 (the first narrowing end position E10) is positioned on the proximal side with respect to the distal end of the second narrowed outer surface 52 (the second narrowing end position E11), and the extending dimension L19 of the first axis parallel outer surface 61 is larger than the extending dimension L20 of the second axis parallel outer surface 62. Consequently, in a case where the first cutting surface 47 moves to a position to be contactable with the lower surface 112 of the acromion 103, the region of the outer surface which faces the first intersecting direction side (the back-surface-side region) in the curved extending section 40, and the tapered section 41 is hard to come in contact with a biological tissue or the like other than a treated target (the lower surface of the acromion 103). Therefore, the first cutting surface 47 is easily movable to the position at which the surface can come in contact with the lower surface 112 of the acromion 103.

Furthermore, in the present embodiment, the first curve start position E14 of the first curve outer surface 55 is positioned on the distal side with respect to the second curve start position E15 of the second curve outer surface 56. Consequently, when the first cutting surface 47 moves to a position to be contactable with the lower surface 112 of the acromion 103, the region of the outer surface which is directed on the first intersecting direction side (the region on the back surface side) in the curved extending section 40 and the tapered section 41 is harder to come in contact with a biological tissue or the like other than a treatment target (the lower surface of the acromion 103). Therefore, the first cutting surface 47 is easily movable to the position at which the surface can come in contact with the lower surface 112 of the acromion 103.

Figure 11:
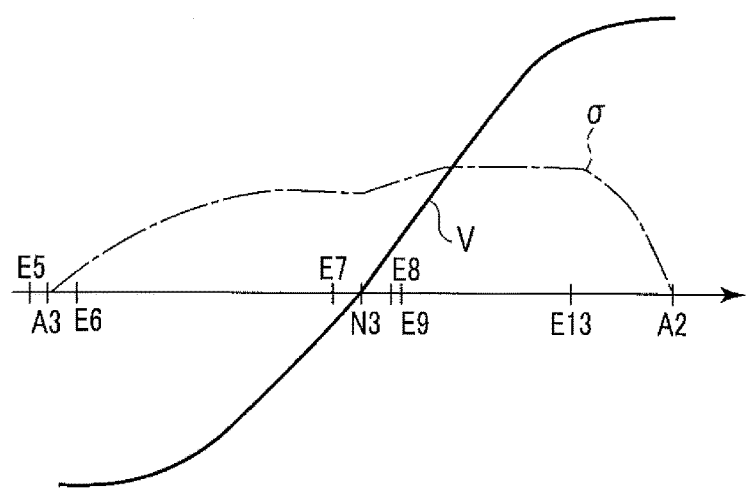
FIG. 11 is a schematic view showing an amplitude of a longitudinal vibration and stress due to an ultrasonic vibration between a second distal vibration antinode and a most distal vibration antinode in a state where the vibrating body unit according to the first embodiment longitudinally vibrates in an established frequency range.

FIG. 11 shows the amplitude V of the longitudinal vibration and stress σ due to the ultrasonic vibration, between the second distal vibration antinode A3 and the most distal vibration antinode A2 in a state where the vibrating body unit 20 longitudinally vibrates in the established frequency range. In FIG. 11, an abscissa shows a position in a longitudinal axis direction and an ordinate shows the amplitude V and the stress σ. Furthermore, in FIG. 11, a solid line shows change of the amplitude V of the longitudinal vibration and a one-dot chain line shows change of the stress σ.

As shown in FIG. 11, in the state where the vibrating body unit 20 longitudinally vibrates in the established frequency range, the tapered section 41 is positioned on the distal side with respect to the most distal side vibration node N3, and an amplitude V of the longitudinal vibration is enlarged in the tapered section 41. For example, the longitudinal vibration in which the amplitude at the vibration antinode is 80 μm is enlarged to the longitudinal vibration in which the amplitude at the vibration antinode is 140 μm or more and 150 μm or less by the tapered section 41. Furthermore, stress σ due to the ultrasonic vibration increases at the vibration node and in a portion in which a sectional area perpendicular to a transmitting direction of the ultrasonic vibration decreases, and the stress becomes zero at the vibration antinode. Therefore, as shown in FIG. 11, the stress σ increases between the vibration node N3 and the distal end (E13) of the tapered section 41.

Here, in the present embodiment, the dimension of the tapered section 41 from the proximal end (E9) to the distal end (E13) in the longitudinal axis direction is larger than the ⅛ wavelength (λ/8) in the state where the vibrating body unit 20 longitudinally vibrates in the established frequency range. Further, in the tapered section 41, the first narrowing dimension L12 between the proximal end (E9) and the first narrowing end position E10 in the longitudinal axis direction is also larger than the ⅛ wavelength in the state where the vibrating body unit 20 longitudinally vibrates in the established frequency range. The dimension of the tapered section 41 from the proximal end (E9) to the distal end (E13) in the longitudinal axis direction increases, so that the stress σ due to the ultrasonic vibration is kept to be substantially constant along the total length between the vibration node N3 and the distal end (E13) of the tapered section 41. That is, between the vibration node N3 and the distal end (E13) of the tapered section 41, the stress is effectively prevented from locally increasing (i.e., generation of a peak is prevented). For example, in the certain example, even when the longitudinal vibration in which the amplitude at the vibration antinode increases (e.g., 80 μm) is transmitted to the proximal end (E9) of the tapered section 41, the stress σ is kept to be substantially uniform at about 300 MPa between the vibration node N3 and the distal end (E13) of the tapered section 41 in the state where the vibrating body unit 20 longitudinally vibrates in the established frequency range (e.g., 46 kHz or more and 48 kHz or less). That is, in the present embodiment, the stress is prevented from locally increasing to about 700 MPa (e.g., at the distal end (E13) of the tapered section 41) between the vibration node N3 and the distal end (E13) of the tapered section 41. The stress σ is prevented from locally increasing, and hence breakage of the ultrasonic probe 8 due to the ultrasonic vibration can effectively be prevented.

Furthermore, in the present embodiment, the cross section gravity center in the cross section perpendicular to the longitudinal axis C shifts from the longitudinal axis C toward the second intersecting direction side in the tapered section 41. Especially, between the first narrowing end position E10 and the second curve start position (the curve proximal end) E15, there increases the shift of the cross section gravity center relative to the longitudinal axis C on the second intersecting direction side. Consequently, in the present embodiment, shift of the center of gravity onto the first intersecting direction side which is caused by the curve of the curved extending section 40 relative to the longitudinal axis direction is canceled by the shift of the center of gravity onto the second intersecting direction side which is caused by the tapered section 41. Consequently, in the state where the ultrasonic vibration of the ultrasonic probe 8 is transmitted toward the distal side, it is possible to decrease generation of irregular vibration (transverse vibration or torsional vibration) except the longitudinal vibration.

In the present embodiment, in the projection from the first width direction (one side of the width direction), the portion between the first curved outer surface 55 and the distal surface 46 is formed into the curved surface of the corner radius R3. Furthermore, in the projection from the first width direction, the portion between the second curved outer surface 56 and the distal surface 46 is formed into the curved surface of the corner radius R4. Further, in the projection from the second intersecting direction (one side of the intersecting direction), each of the portion between the third curved outer surface 57 and the distal surface 46 and the portion between the fourth curved outer surface 58 and the distal surface 46 is formed into the curved surface of the corner radius R5. Consequently, on the distal surface 46 of the ultrasonic probe 8, there decreases a ratio of the surface (the outer surface) perpendicular to the extending direction of the ultrasonic probe 8 (i.e., the vibrating direction of the longitudinal vibration). The ratio of the surface perpendicular to the vibrating direction of the longitudinal vibration decreases, so that even when the ultrasonic probe 8 longitudinally vibrates in the state where the second curved extending section 45 is immersed into the liquid (physiological saline), generation of cavitation in the vicinity of the distal surface 46 is decreased. Due to the decrease of the generation of the cavitation, visibility of an operator in a treatment improves.

Furthermore, in the projecting portion (the exposed portion) of the ultrasonic probe 8 from the distal end of the sheath 7, in the cross section perpendicular to the extending direction, there is formed into the curved surface of the corner radius R6 in each of the portion between the region of the outer surface which faces the first intersecting direction side and the region of the outer surface which faces the first width direction side and the portion between the region of the outer surface which faces the first intersecting direction side and the region of the outer surface which faces the second width direction side. Further, in the projecting portion (the exposed portion) of the ultrasonic probe 8 from the distal end of the sheath 7, in the cross section perpendicular to the extending direction, there is formed into the curved surface of the corner radius R7 in each of the portion between the region of the outer surface which faces the second intersecting direction side and the region of the outer surface which faces the first width direction side and the portion between the region of the outer surface which faces the second intersecting direction side and the region of the outer surface which faces the second width direction side. Consequently, on the outer peripheral surface of the tapered section 41 and the curve extending section 40, any edges are not formed. Therefore, even when the projecting portion (the exposed portion) of the ultrasonic probe 8 from the distal end of the sheath 7 comes in contact with the biological tissue or the like other than the treated target, it is possible to effectively prevent damages on the biological tissue.

(Modification)

In the above-mentioned embodiments or the like, the ultrasonic probe (8) includes the probe main body section (31) which is extended along a longitudinal axis (C), and which is configured to transmit the ultrasonic vibration from a proximal side toward a distal side, and a curved extending section (40) which is provided on the distal side with respect to the probe main body section (31), and which is extended in a state of curving relative to the probe main body section toward a first intersecting direction side in a case where a certain direction intersecting the longitudinal axis (C) is defined as the first intersecting direction (P1). The curved extending section (40) includes a first curved outer surface (55) which faces the first intersecting direction side, a second curved outer surface (57) which faces a second intersecting direction (P2) side in a case where an opposite direction of the first intersecting direction (P1) is defined as the second intersecting direction (P2), a third curved outer surface (57) which faces a first width direction (B1) side in a case where two directions which intersect the longitudinal axis (C) and are perpendicular to the first intersecting direction (P1) and the second intersecting direction (P2) are defined as a first width direction (B1) and a second width direction (B2), and a fourth curved outer surface (58) which faces a second width direction (B2) side. The first cutting surface (47) formed on the second curved outer surface (56), in projection from each of the first width direction (B1) and the second width direction (B2), is formed into a circular shape in which a center (O1) is positioned on the first intersecting direction (P1) side with respect to the curved extending section (40). On the second cutting surface (48) formed on the third curved outer surface (57), the first extending grooves (63A to 63F) is extended along the thickness direction of the curved extending section (40), and on the third cutting surface (49) formed on the fourth curved outer surface (58), the second extending grooves (65A to 65F) is extended along the thickness direction of the curved extending section (40). Each of the relay grooves (71A to 71F) extended on the first cutting surface (48) is continuous with the first extending groove (One of 63A to 63F) at one end, and is continuous with the second extending groove (One of 65A to 65F) at the other end.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe used in a joint, the ultrasonic probe being configured to transmit an ultrasonic vibration so as to treat a treated target in a joint cavity by use of the ultrasonic vibration, the ultrasonic probe comprising:
    a probe main body section which is extended along a longitudinal axis, and the probe main body being configured to transmit the ultrasonic vibration from a proximal side toward a distal side;
    a curved extending section which is provided on the distal side with respect to the probe main body section, the curved extending section being extended in a state of curving relative to the probe main body section toward a first intersecting direction side in a case where a certain direction intersecting the longitudinal axis is defined as a first intersecting direction, the curved extending section including:
        a first curved extending section extended in a state of curving relative to the probe main body section towards the first intersecting direction side; and
        a second curved extending section which is continuous with a distal side of the first curved extending section, the second curved extending section being extended in a state of curving relative to the first curved extending section toward the first intersecting direction side, an acute angle relative to the longitudinal axis in the second curved extending section increasing toward the distal side;
    a first curved outer surface which faces the first intersecting direction side in the curved extending section;
    a second curved outer surface which faces a second intersecting direction side in the curved extending section in a case where an opposite direction of the first intersecting direction is defined as a second intersecting direction;
    a third curved outer surface which faces a first width direction side in the curved extending section in a case where two directions which intersect the longitudinal axis and are perpendicular to the first intersecting direction and the second intersecting direction are defined as a first width direction and a second width direction;
    a fourth curved outer surface which faces a second width direction side in the curved extending section;
    a first cutting surface which forms grooves on the second curved outer surface, the first cutting surface being configured to cut the treated target, in projection from each of the first width direction and the second width direction, the first cutting surface being formed into a circular shape in which a center is positioned on the first intersecting direction side with respect to the curved extending section;
    a second cutting surface which is formed on the third curved outer surface, the second cutting surface being configured to cut the treated target, the second cutting surface including first extending grooves extended along a thickness direction of the curved extending section; and a third cutting surface which is formed on the fourth curved outer surface, the third cutting surface being configured to cut the treated target, the third cutting surface including second extending grooves extended along the thickness direction of the curved extending section.

2. The ultrasonic probe of claim 1, wherein
the first extending grooves are perpendicular to the circular first cutting surface in the projection from the first width direction, and
the second extending grooves are perpendicular to the circular first cutting surface in the projection from the second width direction.

3. The ultrasonic probe of claim 1, wherein an acute angle of a tangent line at a distal end of the second curved outer surface relative to a longitudinal axis direction is 20° or more and 25° or less.

4. The ultrasonic probe of claim 1, wherein the first cutting surface, the second cutting surface and the third cutting surface are provided in the second curved extending section.

5. The ultrasonic probe of claim 1, wherein a first curve start position at which the first curved outer surface starts curving relative to the longitudinal axis toward the first intersecting direction side is positioned on the distal side with respect to a second curve start position at which the second curved outer surface starts curving relative to the longitudinal axis toward the first intersecting direction side.

6. An ultrasonic probe used in a joint, the ultrasonic probe being configured to transmit an ultrasonic vibration so as to treat a treated target in a joint cavity by use of the ultrasonic vibration, the ultrasonic probe comprising:
a probe main body section which is extended along a longitudinal axis, and the probe main body being configured to transmit the ultrasonic vibration from a proximal side toward a distal side;
a curved extending section which is provided on the distal side with respect to the probe main body section, the curved extending section being extended in a state of curving relative to the probe main body section toward a first intersecting direction side in a case where a certain direction intersecting the longitudinal axis is defined as a first intersecting direction;
a first curved outer surface which faces the first intersecting direction side in the curved extending section;
a second curved outer surface which faces a second intersecting direction side in the curved extending section in a case where an opposite direction of the first intersecting direction is defined as a second intersecting direction;
a third curved outer surface which faces a first width direction side in the curved extending section in a case where two directions which intersect the longitudinal axis and are perpendicular to the first intersecting direction and the second intersecting direction are defined as a first width direction and a second width direction;
a fourth curved outer surface which faces a second width direction side in the curved extending section;
a first cutting surface which forms grooves on the second curved outer surface, the first cutting surface being configured to cut the treated target, in projection from each of the first width direction and the second width direction, the first cutting surface being formed into a circular shape in which a center is positioned on the first intersecting direction side with respect to the curved extending section;
a second cutting surface which is formed on the third curved outer surface, the second cutting surface being configured to cut the treated target, the second cutting surface including first extending grooves extended along a thickness direction of the curved extending section; and
a third cutting surface which is formed on the fourth curved outer surface, the third cutting surface being configured to cut the treated target, the third cutting surface including second extending grooves extended along the thickness direction of the curved extending section, wherein
in a range in which the first cutting surface extends, a thickness dimension between the first cutting surface and the first curved outer surface in a thickness direction of the curved extending section is smaller than a width dimension between the third curved outer surface and the fourth curved outer surface in the first width direction and the second width direction.

7. An ultrasonic probe used in a joint, the ultrasonic probe being configured to transmit an ultrasonic vibration so as to treat a treated target in a joint cavity by use of the ultrasonic vibration, the ultrasonic probe comprising:
a probe main body section which is extended along a longitudinal axis, and the probe main body being configured to transmit the ultrasonic vibration from a proximal side toward a distal side;
a curved extending section which is provided on the distal side with respect to the probe main body section, the curved extending section being extended in a state of curving relative to the probe main body section toward a first intersecting direction side in a case where a certain direction intersecting the longitudinal axis is defined as a first intersecting direction;
a first curved outer surface which faces the first intersecting direction side in the curved extending section;
a second curved outer surface which faces a second intersecting direction side in the curved extending section in a case where an opposite direction of the first intersecting direction is defined as a second intersecting direction;
a third curved outer surface which faces a first width direction side in the curved extending section in a case where two directions which intersect the longitudinal axis and are perpendicular to the first intersecting direction and the second intersecting direction are defined as a first width direction and a second width direction;
a fourth curved outer surface which faces a second width direction side in the curved extending section;
a first cutting surface which forms grooves on the second curved outer surface, the first cutting surface being configured to cut the treated target, in projection from each of the first width direction and the second width direction, the first cutting surface being formed into a circular shape in which a center is positioned on the first intersecting direction side with respect to the curved extending section;
a second cutting surface which is formed on the third curved outer surface, the second cutting surface being configured to cut the treated target, the second cutting surface including first extending grooves extended along a thickness direction of the curved extending section; and
a third cutting surface which is formed on the fourth curved outer surface, the third cutting surface being configured to cut the treated target, the third cutting surface including second extending grooves extended along the thickness direction of the curved extending section, wherein:

the probe main body section and the curved extending section are configured to vibrate in an established frequency range in a state where the ultrasonic vibration is transmitted from the probe main body section to the curved extending section; and in a state where the probe main body section and the curved extending section vibrate in the established frequency range, a most distal vibration node positioned most distally among vibration nodes is positioned on the proximal side with respect to a proximal end of the curved extending section.

8. The ultrasonic probe of claim 7, further comprising:
a tapered section which is provided between the probe main body section and the curved extending section in the longitudinal axis direction, and in which a sectional area perpendicular to the longitudinal axis decreases from the proximal side toward the distal side, the tapered section being configured to vibrate together with the probe main body section and the curved extending section in the established frequency range in the state where the ultrasonic vibration is transmitted from the probe main body section to curved extending section, wherein in the state where the probe main body section, the curved extending section and the tapered section vibrate in the established frequency range, the most distal vibration node is positioned on the proximal side with respect to a proximal end of the tapered section, and a ⅛ wavelength of the vibration is smaller than a taper dimension from the proximal end of the tapered section to a distal end of the tapered section in the longitudinal axis direction.

9. An ultrasonic probe used in a joint, the ultrasonic probe being configured to transmit an ultrasonic vibration so as to treat a treated target in a joint cavity by use of the ultrasonic vibration, the ultrasonic probe comprising:

a probe main body section which is extended along a longitudinal axis, and the probe main body being configured to transmit the ultrasonic vibration from a proximal side toward a distal side;

a curved extending section which is provided on the distal side with respect to the probe main body section, the curved extending section being extended in a state of curving relative to the probe main body section toward a first intersecting direction side in a case where a certain direction intersecting the longitudinal axis is defined as a first intersecting direction;

a first curved outer surface which faces the first intersecting direction side in the curved extending section;

a second curved outer surface which faces a second intersecting direction side in the curved extending section in a case where an opposite direction of the first intersecting direction is defined as a second intersecting direction;

a third curved outer surface which faces a first width direction side in the curved extending section in a case where two directions which intersect the longitudinal axis and are perpendicular to the first intersecting direction and the second intersecting direction are defined as a first width direction and a second width direction;

a fourth curved outer surface which faces a second width direction side in the curved extending section;

a first cutting surface which forms grooves on the second curved outer surface, the first cutting surface being configured to cut the treated target, in projection from each of the first width direction and the second width direction, the first cutting surface being formed into a circular shape in which a center is positioned on the first intersecting direction side with respect to the curved extending section;

a second cutting surface which is formed on the third curved outer surface, the second cutting surface being configured to cut the treated target, the second cutting surface including first extending grooves extended along a thickness direction of the curved extending section;

a third cutting surface which is formed on the fourth curved outer surface, the third cutting surface being configured to cut the treated target, the third cutting surface including second extending grooves extended along the thickness direction of the curved extending section;

a first narrowed outer surface which faces the first intersecting direction side, and which is provided between the probe main body section and the first curved outer surface in the longitudinal axis direction, a first distance from the longitudinal axis in the first intersecting direction decreasing from the proximal side toward the distal side on the first narrowed outer surface;

a second narrowed outer surface which faces the second intersecting direction side, and which is provided between the probe main body section and the second curved outer surface in the longitudinal axis direction, a second distance from the longitudinal axis in the second intersecting direction decreasing from the proximal side toward the distal side on the second narrowed outer surface;

a first axis parallel outer surface that faces the first intersecting direction side, and that is continuous between the first narrowed outer surface and the first curved outer surface in the longitudinal axis direction, the first axis parallel outer surface being extended in parallel with the longitudinal axis; and a second axis parallel outer surface that faces the second intersecting direction side, and that is continuous between the second narrowed outer surface and the second curved outer surface in the longitudinal axis direction, the second axis parallel outer surface being extended in parallel with the longitudinal axis.

10. The ultrasonic probe of claim 9, wherein a first extending dimension of the first axis parallel outer surface in the longitudinal axis direction is larger than a second extending dimension of the second axis parallel outer surface in the longitudinal axis direction.

11. The ultrasonic probe of claim 9, wherein a first narrowing angle of the first narrowed outer surface relative to the longitudinal axis direction is larger than a second narrowing angle of the second narrowed outer surface relative to the longitudinal axis direction.

12. The ultrasonic probe of claim 9, wherein a distal end of the first narrowed outer surface is positioned on the proximal side with respect to a distal end of the second narrowed outer surface.

* * * * *